United States Patent [19]  
Robl

[11] Patent Number: 5,072,023  
[45] Date of Patent: Dec. 10, 1991

[54] PROCESS FOR PREPARING HIGHLY SUBSTITUTED PHENYLS

[75] Inventor: Jeffrey A. Robl, Holland, Pa.

[73] Assignee: E. R. Squibb & Sons, Inc., Princeton, N.J.

[21] Appl. No.: 480,470

[22] Filed: Feb. 15, 1990

[51] Int. Cl.$^5$ ............................................. C07C 69/88
[52] U.S. Cl. ........................................ 560/67; 560/71; 560/59
[58] Field of Search .............................. 560/67, 71, 59

[56] References Cited

PUBLICATIONS

F. M. Hauser et al., "A New Procedure for Regiospecific Syntheses of Benzopyran-1-One", J. Org. Chem. 53 (1988), 4676–4681.
F. M. Hauser et al., "Syntheses of α-and β- Sorigenin Methyl Esters", J. Org. Chem. 42 (1977), 4155–4157.
A. M. Echavarren et al., "Palladium-Catalyzed Coupling of Aryl Triflates with Organostannes", J. Am. Chem. Soc. 109 (1987), 5478–5486.
F. M. Hauser et al., "Preparation of Ethyl 1-Hydroxy-2-Naphthoates from 1H≧2-Benzopyran-1-Ones: A New Method", J. Heterocyclic Chem. 15 (1978), 1535.
R. A. Abramovitch et al., "New Methods of Arylation", Tetrahedron 44 (1988), 3039.
O. Toussaint et al., "The Copper (I)-Catalyzed Decarboxylation of Malonic Acids: A New Mild and Quantitative Method", Synthesis (1986), 1029.
P. Brownbridge, "Silyl Enol Ethers in Syntheses-Part I", Synthesis (1983), 1–28.
P. Brownbridge, "Silyl Enol Ethers in Synthesis-Part II", Synthesis, (1983) 85–104.
G. E. Stokker et al., "3-Hydroxy-3-Methylglutaryl-Coenzyme A Reductase Inhibitors. 1. Structural Modification of etc...", J. Med. Chem. 28 (1985), 347–358.
A. P. Krapcho et al., "Synthetic Applications and Mechanism Studies of the Decarbalkoxylations of Geminal Diesters and Related Systems Effected in Me$_2$SO by Water and/or etc. . .", J. Org. Chem. 43 (1978), 138–147.
G. E. Stokker et al., "3-Hydroxy-3-Methylglutaryl-Coenzyme A Reductase Inhibitors. 3. 7-(3-,5-Disubstituted)1,1' etc...", J. Med. Chem. 29 (1986), 170–181.
W. F. Hoffman et al., "3-Hydroxy-3-Methylglutaryl-Coenzyme A Reductase Inhibitors. 2. Structural Modification of etc...", Journal of Medicinal Chemistry 2 (1986), 159–169.
G. E. Stokker et al., "3-Hydroxy-3-Methylglutaryl-Coenzyme A Reductase Inhibitors. 5. 6-(-Fluoren-9-yl)- and 6-(Fluoren etc...", Journal of Medicinal Chemistry 29 (1986), 852–855.

Primary Examiner—Paul J. Killos  
Attorney, Agent, or Firm—Timothy J. Gaul

[57] ABSTRACT

A process is described in which a lactone

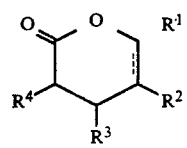

is reacted with an alkylester $X^1$—$CH_2$ and an oxidizing or dehydrogenating agent to form the phenol ester

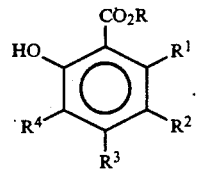

3 Claims, No Drawings

PROCESS FOR PREPARING HIGHLY SUBSTITUTED PHENYLS

FIELD OF INVENTION

The present invention relates to processes for preparing highly substituted phenyls, including phenylaldehydes, phenylmethanols and phenylesters, which are useful inter alia as intermediates in the preparation of inhibitors of 3-hydroxy-3-methyl glutaryl coenzyme A (HMG CoA) reductase. HMG CoA reductase is an enzyme used in cholesterol biosynthesis, and its inhibitors are well known to be useful antihypercholesterolemic agents.

BACKGROUND OF THE INVENTION

Several references have reported highly substituted phenyls to be HMG CoA reductase inhibitors. Stokker et al., J. Med. Chem. 28 (1985), 347; Hoffman et al., J. Med. Chem. 29 (1986), 159; Stokker et al., J. Med. Chem. 29 (1986), 170; Stokker et al., J. Med. Chem. 29 (1986), 852; U.S. patent application 182,710, filed April 18, 1988. Such highly substituted phenyls are generally difficult to prepare because of a lack of regio control—i.e., an inability to selectively link substituents to the desired carbon atoms in the phenyl ring. The art would benefit from processes for preparing highly substituted phenyls in high yields.

BRIEF DESCRIPTION OF THE INVENTION

In accordance with the present invention, a process is provided for preparing a phenol ester of the formula

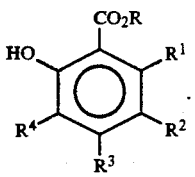

from a lactone of the formula

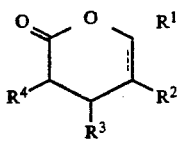

in which the lactone II is reacted with an alkylester of the formula

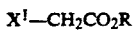

$$X^1-CH_2CO_2R \qquad \text{III}$$

and an oxidizing or dehydrogenating agent.

It is preferred that the lactone II first be reacted with the alkylester III to form a cyclohexenone ester of the formula

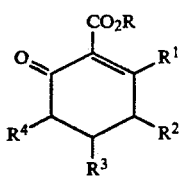

which is then reacted with the oxidizing or dehydrogenating agent to obtain phenol ester compound I.

In compound I and throughout this specification, the symbols above are as defined below:

R is lower alkyl;

$R^1$, $R^2$, $R^3$, and $R^4$ are each independently hydrogen, lower alkyl, cycloalkyl, aryl, aralkyl, or aralkoxy; and $X^1$ is alkali metal or zinc halide.

DETAILED DESCRIPTION OF THE INVENTION

The term "alkyl" as employed herein alone or as part of another group includes straight chain hydrocarbons having 1 to 12 carbons (preferably 1 to 7 carbons) in the normal chain and the various branched isomers thereof, such as methyl, ethyl, propyl, isopropyl, butyl, t-butyl, isobutyl, pentyl, hexyl, isohexyl, heptyl, 4,4dimethylpentyl, octyl, 2,2,4-trimethylpentyl, nonyl, decyl, undecyl, dodecyl, and the like, as well as such groups including one or more substituents selected from halo (such as F, Br, Cl, and I), $CF_3$, alkoxy, hydroxy, alkylamino, alkanoylamino, carbonylamino, nitro, cyano, mercapto, and alkylthio.

The term "lower alkyl" refers to alkyl groups having 1 to 4 carbon atoms.

The terms "aryl" and "ar" as employed herein refer to monocyclic or bicyclic aromatic groups containing 6 to 10 carbons in the ring portion, such as phenyl, naphthyl, substituted phenyl or substituted naphthyl, wherein the substituent on either the phenyl or naphthyl may be halogen (Cl, Br or F), $CF_3$, 1, 2 or 3 lower alkoxy groups, 1, 2 or 3 hydroxy groups, 1, 2 or 3 phenyl groups, 1, 2 or 3 alkanoyloxy groups, 1, 2 or 3 benzoyloxy groups, 1, 2 or 3 halophenyl groups, 1, 2 or 3 alkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, and 1, 2 or 3 thiol groups, with the aryl group preferably containing 3 substituents.

The terms "aralkyl", "aryl-alkyl" or "aryl-lower alkyl" as used herein alone or as part of another group refer to groups having at least one alkyl and at least one aryl group as defined above, such as benzyl, as well as such groups having one or more substituents selected from cycloalkyl, alkylcycloalkyl, amino, oxy, alkoxy, and adamantyl, wherein the aralkyl, aryl-alkyl, or aryl-lower alkyl group is attached to the remainder of any compound by way of a carbon atom in the alkyl portion of the group.

The terms "lower alkoxy", "alkoxy", "aryloxy" or "aralkoxy" as employed herein alone or as part of another group include any of the above lower alkyl, alkyl, aralkyl or aryl groups linked to an oxygen atom.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, wherein such groups may be substituted with 1 or 2 halogens, 1 or 2 lower alkyl groups and/or 1 or 2 lower alkoxy groups.

The terms "halogen" or "halo" as used herein refer to chlorine, bromine, fluorine, and iodine, with chlorine and fluorine being preferred.

The processes of the present invention are summarized in the Reaction Scheme set out hereinafter.

As shown in the Reaction Scheme, dialkyl malonate ester XIV is reacted with $R^3$-aldehyde XVIII in a molar ratio from about 0.5:1 to about 2:1 to form alkylidene XIX. (In these compounds and throughout this specification, $X^3$ and $X^4$ are each independently lower alkyl.) This reaction may be effected by Knoevenagel condensation under generally known conditions; for example, treatment with catalytic piperidine and acetic acid or molecular sieves in benzene or methylene chloride at about 25° to 110° C.

Alkylidene XIX is then reacted with enolether XX wherein $X^5$ is alkali metal, silyl, or alkylsilyl. When $X^5$ is alkali metal, enolether compound XX may be generated by proton abstraction of the corresponding ketone ($R^2CH_2COR^1$) in an aprotic solvent (e.g., tetrahydrofuran or ethyl ether) at about −78° to 0° C. with a base such as lithium diisopropylamide, lithium isopropylcyclohexylamide, lithium tetramethylpiperidide, lithium bistrimethylsilylamide, or sodium bistrimethylsilylamide. When $X^5$ is alkali metal, alkylidene XIX may be reacted by Michael addition with enolether XX in a molar ratio from about 1:1 to about 0.5:1, in such solvents as tetrahydrofuran or diethyl ether at about −78° to 0° C., to form the $R^{1-3}$ diester adduct XVI.

When $X^5$ is silyl or alkylsilyl (e.g., trimethylsilyl, t-butyldimethylsilyl), enolether XX may be derived from the corresponding ketone ($R^2CH_2COR^1$) by procedures described in Brownbridge, P., Synthesis (1983), 1. When $X^5$ is silyl or alkylsilyl, enolether XX may be reacted with alkylidene XIX under acidic conditions (e.g., boron trifluoride, titanium tetrachloride, or stannous chloride) in an organic solvent (e.g., methylene chloride, tetrahydrofuran, toluene, or diethyl ether) at about −78° to 25° C. to form the $R^{1-3}$ diester adduct XVI. For further reaction conditions, see Brownbridge, P., Synthesis (1983), 85. Using the same temperatures and solvents, adduct XVI can also be formed under basic conditions (e.g., tetrabutylammonium fluoride, cesium fluoride). For further reaction conditions, see Brownbridge, P., Synthesis (1983), 85.

$R^{1-3}$ diester adduct XVI may also be obtained by reaction of dialkyl malonate ester XIV and α, β-unsaturated enone XV in a molar ratio from about 0.5:1 to about 2:1. This reaction can be effected at about 0° to 100° C. by treatment with, for example:

sodium ethoxide in ethanol,
sodium t-butoxide in t-butanol,
Triton B in water and dioxane,
zinc chloride in benzene, or
piperidine in benzene.

$R^{1-4}$ diester XVII is obtained by alkylation or arylation or $R^{1-3}$ diester XVI. When the alkylating agent X $$R^5Z \qquad\qquad X$$

is used, wherein Z is halo, —OSO₂-lower alkyl, —OSO₂-aryl, or —OSO₂CF₃, the reaction takes place in the presence of a suitable base (e.g., lithium diisopropylamide, sodium ethoxide, sodium hydride, sodium amide, potassium carbonate, thallium ethoxide, Na° metal) at about -78° to 60° C. in a suitable inert solvent (e.g., tetrahydrofuran, diethyl ether, dimethylformamide, toluene). When the arylating agent X is used, wherein Z is Pb(acetate)₃, the reaction takes place in the presence of a suitable base (e.g., pyridine) and solvent (e.g., tetrahydrofuran) following procedures described in Piney, J. T. and Rowe, R. A. Tet. Lett. 1980, 965. In addition, activated esters may be arylated with aryl bismuth compounds under conditions described in Abramovitch, R. A., Tetrahedron 44 (1988), 3039.

Diacid XXI is obtained by saponification of $R^{1-4}$ diester XVII using, for example, an alkali metal hydroxide such as sodium or potassium hydroxide at about 0° to 100° C. in an inert solvent (e.g., water, methanol, ethanol, or dioxane).

Monoacid XXII is obtained by decarboxylation of diacid XXI, using such reactants as concentrated hydrochloric acid or sulfuric acid (heated to about 100° to 250° C.) and cuprous oxide in acetonitrile. For further reaction conditions, see Toussaint et al., Synthesis (1986), 1029. Alternatively, $R^{1-4}$ diester XVII is converted to an ester (e.g., with lithium chloride in dimethylsulfoxide and water, heated to about 25° to 100° C)., followed by saponification under the conditions described above to obtain monoacid XXII. For further reaction conditions, see Krapcho, A. et al., J. Org. Chem. 43 (1978), 138.

Monoacid XXII undergoes dehydrative cyclization to form unsaturated lactone II, possibly as a mixture of double bond isomers, depending on the identity of $R^1$ and $R^2$. The reaction may be effected by, for example, catalytic perchloric acid and acetic anhydride in ethyl acetate; see Hauser, F. M. et al., J. Org. Chem. 53 (1988), 4676. Alternatively, the dehydrative cyclization may be effected by concentrated sulfuric acid in a molar ratio from about 1:1 to about 20:1 sulfuric acid to monoacid XXII, heated to about 25° to 100° C.

Lactone II is reacted with ester anion III in a molar ratio of about 1:2 to obtain cyclohexenone ester IV. When $X^1$ is zinc halide, ester anion III is generated under Reformatsky conditions from ester anion III where $X^1$ is halide in a solvent such as benzene at about 25° to 80° C. in the presence of zinc. When lactone II is present under these conditions, cyclohexenone ester IV is formed. For further reaction conditions, see Hauser et al., J. Org. Chem. 42 (1977), 4155. When $X^1$ is alkali metal, compounds II and III may be reacted in an organic solvent or solvent mixture (e.g., tetrahydrofuran, ethyl ether, dimethylsulfoxide) at about −20° to 0° C. and quenched with acetic acid. For further reaction conditions, see Hauser et al., J. Heterocyclic Chem. 15 (1978), 1535.

Cyclohexenone ester IV is then treated with an oxidizing or dehydrogenating agent to form phenol ester I. Oxidizing agents (e.g., 2,3dichloro-5,6-dicyano-1,4-benzoquinone (DDQ), chloranil, m-iodylbenzoic acid with diphenyl diselenide, iodosylbenzene, manganese (III) acetate) may be used at about 0° to 150° C. in an organic solvent (e.g., benzene, toluene, dioxane, methanol, methylene chloride, acetic acid). Dehydrogenating agents (e.g., platinum, palladium, rhodium) may be used in an inert solvent (e.g., Decalin®) at about 150° to 250° C.

Alternatively, phenol ester I can be prepared by treating lactone II with an oxidizing or dehydrogenating agent to form lactone XXIII. For example, lactone II is treated with DDQ in an inert solvent such as toluene or dioxane or by selenation of compound II with phenylselenyl chloride, followed by treatment with hydrogen peroxide. Lactone XXIII is then treated under the same conditions described above for treatment of lactone II to form cyclohexenone ester IV. The former process (lactone II→cyclohexenone ester IV→ phenol ester I) results in a much higher yield of phenol ester I and is therefore preferred.

Phenol ester I is then reacted with a sulfonating agent (e.g., trifluoromethanesulfonic anhydride, trifluoromethansulfonyl chloride) to form sulfonate-substituted phenylester V. This reaction may take place in an aprotic solvent (e.g., pyridine, dichloromethane, trichloromethane, toluene) at about $-20°$ to $25°$ C., optionally in the presence of such bases as pyridine, triethylamine, ethyldiisopropylamine, and 1,8-bis(dimethylamino)naphthalene.

Sulfonate-substituted phenylester V is then reacted with substituted stannane VI(A)

$$R^5Sn(R^6)_3 \qquad VI(A)$$

in a molar ratio from about 0.5:1 to about 1:1 to form multi-substituted phenylester VII. This reaction can be effected in the presence of a palladium catalyst (e.g., tetrakis(triphenylphosphine)palladium (O), bis(triphenylphosphine)palladium (II) dichloride, bis(triphenylphosphine)benzyl palladium chloride) at about $0°$ to $120°$ C. in such organic solvents as dimethylformamide, tetrahydrofuran, toluene and dioxane. For further reaction conditions, see Echavarren et al., J. Am. Chem. Soc. 109 (1987), 5478.

Alternatively, sulfonate-substituted phenylester V may be reacted with cuprates such as compound VI(B)

$$(R^5)_2CuM \qquad VI(B)$$

(e.g., $(R^5)_2CuLi$ and $(R^5)_2CuCNLi_2$) in a molar ratio of about 1:1 to about 0.2:1 in solvents such as tetrahydrofuran or diethyl ether at temperatures of $-78°$ to $25°$ C. to form multi-substituted phenylester VII. For further reaction conditions, see Lipshutz et al., Tetrahedron (1984), 5018–5019; McMurry, J. E. and Mohanraj, S., Tetrahedron Letters (1983), 2723.

Alternatively, compound V may be reacted with an amine base (e.g., tributylamine) and formic acid in the presence of a palladium catalyst (e.g., bis(triphenylphosphine)palladium (II)chloride) in an organic solvent (e.g., dimethylformamide) at to about $25°$ to $125°$ C. to form compound VII wherein $R^5$ is hydrogen. To form compound VII wherein $R^5$ is formyl, compound V is reacted with carbon monoxide and a trialkyl stannanyl hydride (e.g., tributylstannane) in the presence of a palladium catalyst (e.g., bis(triphenylphosphine)palladium (II) chloride) in an inert solvent (e.g., toluene or tetrahydrofuran) at about $25°$ to $100°$ C. To form compound VII wherein $R^5$ is carboxylester or carboxamide, compound V is reacted with carbon monoxide and an alcohol or amine respectively in the presence of a palladium catalyst (e.g., palladium acetate) and phosphine ligand (e.g., triphenylphosphine, 1,3-bis(diphenylphosphino)propane) in an organic solvent (e.g., dimethylsulfoxide, dimethylformamide) at about $25°$ to $100°$ C. When $R^5$ in compound VII is desired to be cyano, compound V is reacted with a cyanide (e.g., potassium cyanide) in the presence of a nickel catalyst (e.g., tetrakis (triphenylphosphino) nickel (O) in an inert solvent (e.g., acetonitrile). To form compound VII wherein $R^5$ is alkanoyl, compound V is reacted with an $\alpha$(alkoxyvinyl)tributyltin such as ($\alpha$-ethoxyvinyl)tributyltin in the presence of a palladium catalyst (e.g., bis(triphenylphosphine)palladium (II) chloride) in an inert solvent (e.g., toluene) at about $25°$ to $100°$ C., followed by aqueous acidic treatment.

Multi-substituted phenylester VII may be reduced to multi-substituted phenylmethanol VIII at about $-78°$ to $60°$ C. by any of several reagents, including:

lithium aluminum hydride in ethyl ether or tetrahydrofuran, diisobutylaluminum hydride in toluene, and lithium triethylborohydride in tetrahydrofuran.

In turn, phenylmethanol VIII may be oxidized to phenylaldehyde IX to about $-78°$ to $25°$ C. by any of several reagents, including:

oxalyl chloride, dimethylsulfoxide, and triethylamine in methylene chloride, pyridinium chlorochromate in methylene chloride, and tetrapropylammonium peruthenate and 4-methylmorpholine N-oxide in methylene chloride.

In compounds V through IX and throughout this specification, the symbols are as defined below:

$R^5$ is hydrogen, lower alkyl, cycloalkyl, aryl, aralkyl, or aralkoxy:

$R^6$ is lower alkyl, cycloalkyl, aryl, or aralkyl;

$X^2$ is halo or trifluoromethyl; and

M is lithium or $-CN(lithium)_2$.

Alternatively, phenol ester I is reacted with an alkylating or arylating agent such as compound X in a molar ratio from about 1:1 to about 0.5:1 to form oxy-substituted phenylester XI. When alkylating agent X is used, the reaction takes place in the presence of a base (e.g., potassium carbonate, sodium hydroxide, sodium hydride, Na° metal, thallium ethoxide at about $0°$ to $60°$ C. in an organic solvent (e.g., acetone, dimethylformamide, dimethylsulfoxide, tetrahydrofuran, toluene, t-butanol). Arylating agent X, wherein $R^5Z$ is (Aryl)$_3$Bi(OAc)$_2$ (wherein Ac is acetyl), (Aryl)$_4$Bi(OCOCF$_3$), (Aryl)$_2$IBr, or Aryl-halo, may be reacted with phenol ester I to give oxy-substituted phenylester XI. For specific reaction conditions for these arylating agents, see Barton, D. H. R. et al., Tet. Lett. (1986), 3619; Barton, D. H. R. et al., J. Chem. Soc., Chem. Comm. (1981), 503; Bacon, R. G. R. and Stewart, O. J., J. Chem. Soc. (1965), 4953; Crowder, J. R. et al., J. Chem. Soc. (1963), 4578.

Oxyphenylmethanol XII and oxyphenylaldehyde XIII are prepared following the procedures described above for compounds VII and IX, respectively. The references noted in the Background of the Invention describe the use of phenylaldehydes such as compounds IX and XIII in preparation of HMG-CoA reductase inhibitors.

The invention will now be further described by the following working examples. These examples are illustrative rather than limiting. In the examples, a compound prepared in part 1-A will be referred to as "compound 1-A" as a shorthand reference, and likewise for all of the compounds prepared. All temperatures in the examples are in degrees Celsius.

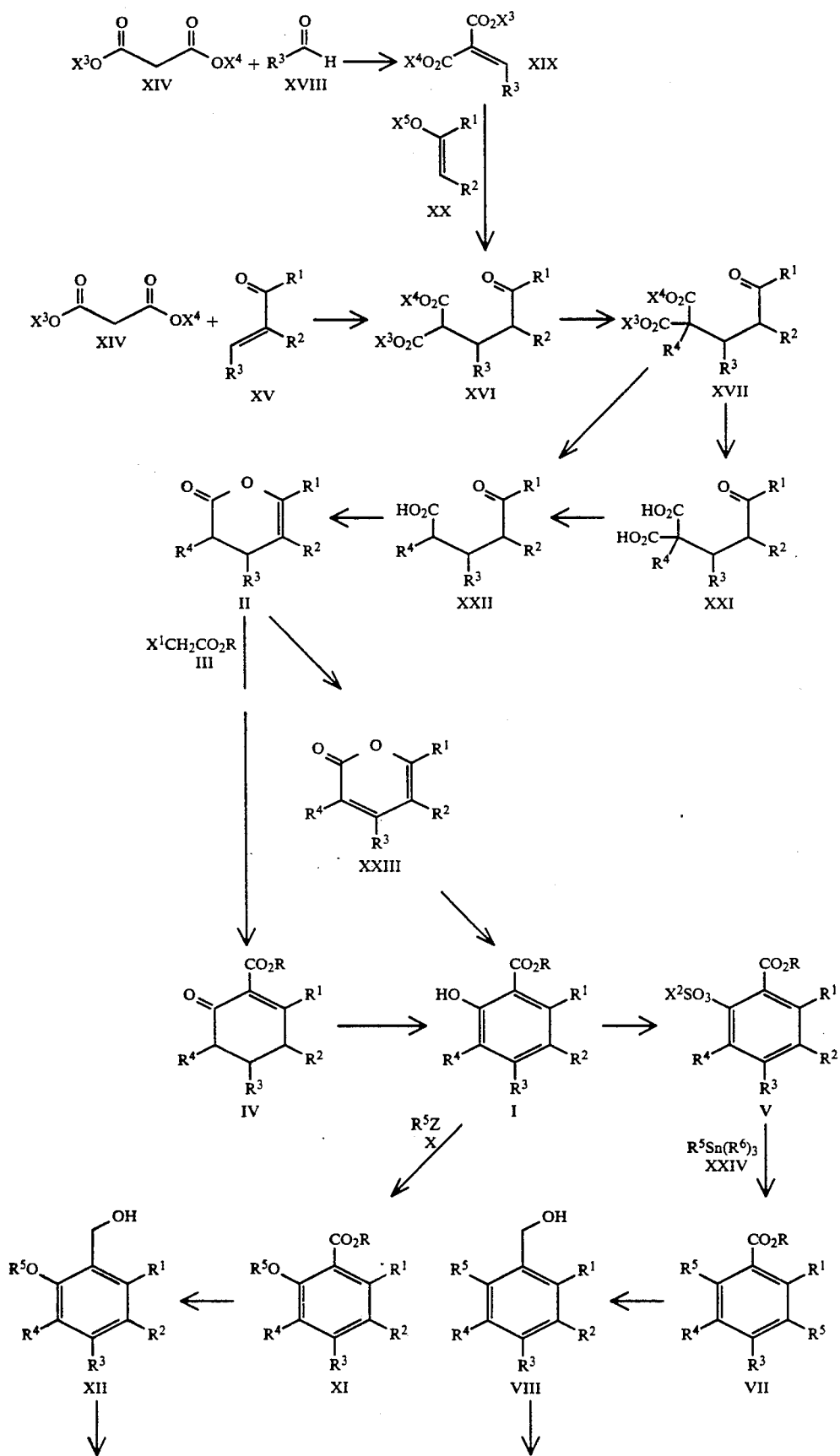
Reaction Scheme

-continued
Reaction Scheme

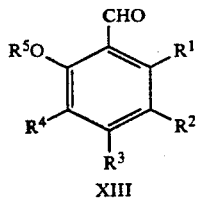

XIII

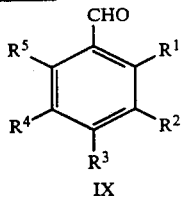

IX

EXAMPLE 1

[1-(1,1-Dimethylethyl)-4-methyl-3-oxopentyl]-propanedioic acid, diethyl ester

1-A. 2,6,6-Trimethyl-4-hepten-3-one

A solution of trimethylacetaldehyde (20.00 gm, 230 mmol) and 3-methyl-2-butanone (20.00 gm, 230 mmol) in absolute ethanol (50 mL) was treated with a solution of sodium ethoxide in ethanol (21% by weight, 11.3 gm, 35 mmol). After stirring at room temperature for 4 hours, most of the ethanol was removed on the rotovap and the residue was partitioned between diethyl ether and 50% saturated ammonium chloride. The aqueous layer was removed and the diethyl ether layer was washed with water and brine, then dried (magnesium sulfate), filtered and stripped to give a yellow liquid. The liquid was distilled (boiling point. 191°-195° C. at atmospheric pressure) to give crude compound 1-A as a pale yellow liquid. The distillate was flash chromatographed (Merck silica gel, 10% ethyl acetate in hexane) to provide pure enone compound 1-A (5.745 gm, 16%).

Thin layer chromatography: $R_f = 0.35$ (20% ethyl acetate in hexane).

1-B.
[1-(1,1-Dimethylethyl)-4-methyl-3-oxopentyl]-propanedioic acid, diethyl ester A solution of compound 1-A (5.69 gm, 36.9 mmol) and diethyl malonate (7.936 gm, 49.5 mmol) in absolute ethanol (40 mL) was treated with a solution of sodium ethoxide in ethanol (21% by weight, 1.58 gm, 4.9 mmol). An additional 1.55 gm sodium ethoxide solution was added 4 hours later. After stirring at room temperature for 40 hours, the mixture was poured into 50% saturated ammonium chloride and extracted with ethyl ether. The ethyl ether extract was washed with water and brine, then dried (magnesium sulfate), filtered and stripped. The resulting oil was transferred to a round bottom flask fitted with a short path distillation apparatus and was subsequently heated at 85° C., 0.4 mm Hg in order to remove most of the unreacted diethyl malonate. The residue was flashed (Merck SiO2, 10% ethyl acetate in hexane) to give diester Example 1 compound as a colorless liquid (8.152 gm, 70%).

Thin layer chromatography: $R_f = 0.43$ (20% ethyl acetate in hexane).

EXAMPLE 2

4-(1,1-Dimethylethyl)-2-hydroxy-6-(1-methylethyl)benzoic acid, ethyl ester

2-A. 3-(1,1-Dimethylethyl)-6-methyl-5-oxoheptanoic acid

A solution of diester Example 1 (8.032 gm, 25.5 mmol) in ethanol (50 mL) was treated with a solution of potassium hydroxide (7.08 gm, 126 mmol) in water (50 mL). The mixture was refluxed for 1.5 hours, during which time most of the ethanol was distilled off. The solution was cooled to room temperature and the aqueous solution was washed with diethyl ether. The diethyl ether layer was discarded and the aqueous layer was made acidic with concentrated hydrochloric acid. The mixture was extracted twice with diethyl ether and the pooled extracts were washed with water and brine, then dried (magnesium sulfate), filtered and stripped to afford the crude intermediate diacid ($R_f = 0.60$ in 8:1:1-methylene chloride:acetic acid:methanol) as a colorless oil.

A mixture of the crude diacid and cuprous oxide (380 mg, 2.6 mmol) was dissolved in acetonitrile (100 mL) and subsequently refluxed under argon for 1.5 hours. The cooled solution was stripped on the rotovap to remove nearly all of the acetonitrile. The residue was diluted with water and treated with 10% hydrochloric acid (30 mL), then extracted with diethyl ether. The diethyl ether extract was washed with water and brine, then dried (magnesium sulfate), filtered and stripped to give compound 2-A as a colorless liquid (5.46 gm, 100%).

Thin layer chromatography: $R_f = 0.52$ (1:1acetone:-hexane).

2-B.
4-(1,1-Dimethylethyl)-3,4-dihydro-6-(1methylethyl)-2H-pyran-2-one and

2-C.
4-(1,1-Dimethylethyl)tetrahydro-6-(1methylethylidene]-2H-pyran-2-one

A solution of compound 2-A (5.425 gm, 25.3 mmol) in ethyl acetate (10 mL) was added to a stirring solution of ethyl acetate (90 mL), acetic anhydride (10.1 gm, 99 mmol), and 70% perchloric acid (162 mg). After 5 minutes, the solution was diluted with diethyl ether and quenched with both saturated sodium bicarbonate and solid sodium bicarbonate. The organic layer was separated and washed with brine, then dried (magnesium sulfate), filtered and stripped to yield an oil. The oil was chromatographed (flash, Merck silica gel, 20% ethyl acetate in hexane) to yield a mixture of compounds 2-B and 2-C (4.68 gm, 94%) in an 88:12 ratio as a liquid.

Thin layer chromatography: $R_f = 0.44$ 0.32 (20% ethyl acetate in hexane).

2-D.
4-(1,1-Dimethylethyl)-2-(1-methylethyl)-6oxo-1-cyclohexene-1-carboxylic acid, ethyl ester A cold (0° C.) solution of isopropylcyclohexylamine (7.80 mL, 6.70 gm, 47.4 mmol) in dry tetrahydrofuran (90 mL) was treated with n-butyl lithium (2.5 M in hexane, 19.0 mL, 47.5 mmol). After stirring at 0° C. for 25 minutes and at room temperature for 5 minutes, the solution was cooled to −78° C. and treated dropwise with ethyl acetate (4.65 mL, 4.19 gm, 47.6 mmol).

Thirty minutes after the addition, the mixture was added rapidly via cannula to a cold (0° C.) solution of compounds 2-B and 2-C (7:1 mixture, 4.660 gm, 23.7 mmol) in tetrahydrofuran (50 mL) and dimethylsulfoxide (50 mL). The mixture was stirred at 0° C. for 30 minutes, quenched with glacial acetic acid (50 mL), and stirred at room temperature for 20 hours. The tetrahydrofuran was removed on the rotovap and the residue was poured into diethyl ether and washed three times with water. The aqueous layers were back-extracted once with diethyl ether and the pooled ethereal layers were washed with brine. The solution was dried (magnesium sulfate), filtered and stripped to give an oil which was subjected to flash chromatography (Merck silica gel, 20% ethyl acetate in hexane), providing compound 2-D (5.485 gm, 87%) as a pale yellow oil.

Thin layer chromatography: $R_f=0.27$ (20% ethyl acetate in hexane).

2-E.
4-(1,1-Dimethylethyl)-2-hydroxy-6-(1methylethyl)benzoic acid, ethyl ester

A mixture of compound 2-D (5.480 gm, 24.4 mmol) and 2,3-dichloro-5,6-dicyano-1,4benzoquinone (7.01 gm, 30.9 mmol) in dry dioxane (200 mL) was heated at 85° C. After 17 hours of heating, an additional 1.40 gm 2,3-dichloro-5,6dicyano-1,4-benzoquinone was added to the dark mixture and the temperature was raised to 105° C. After 42 hours of heating, the solution was cooled to room temperature, diluted with hexane and filtered through a plug of silica gel. The filtrate was stripped and the residue was flashed (Merck, silica gel, 10% ethyl acetate in hexane) to give pure phenol Example 2 (2.904 gm, 49%) as a colorless oil.

Thin layer chromatography: $R_f=0.54$ (20% ethyl acetate in hexane).

EXAMPLE 3

5-(1,1-Dimethylethyl)-4'-fluoro-3-(1-methylethyl)[1,1'-biphenyl]-2-carboxaldehyde 3-A.
4-(1,1-Dimethylethyl)-6-(1-methylethyl)2[[(trifluoromethyl)sulfonyl]oxy]benzoic acid, ethyl ester A cold (0° C.) solution of Example 2 (2.870 gm, 10.13 mmol) in dry pyridine (7 mL) was treated dropwise with trifluoromethanesulfonic anhydride (2.00 mL, 3.35 gm, 11.9 mmol). The yellow solution was stirred at 0° C. for one hour and at room temperature for 17 hours. The mixture was poured into water and extracted with diethyl ether. The diethyl ether extract was washed with water, 10% hydrochloric acid, water, and brine, dried (magnesium sulfate), filtered and stripped. The residue was flashed (Merck silica gel, 5% ethyl acetate in hexane) to give compound 3-A (3.797 gm, 95%) as a pale yellow oil.

Thin layer chromatography: $R_f=0.41$ (10% ethyl acetate in hexane).

3-B. 5-(1,1-Dimethylethyl)-4'-fluoro-3-(1methylethyl)[1,1'-biphenyl]-2-carboxylic acid, ethyl ester A mixture of compound 3-A (3.503 gm, 8.84 mmol), (4-fluorophenyl)-tri-n-butylstannane (4.908 gm, 12.7 mmol), lithium chloride (1.202 gm, 28.4 mmol), and a few crystals of 2,6-di-tertbutyl-4-methylphenol in dry dimethylformamide (45 mL) was treated with bis(triphenylphosphine) palladium dichloride (192 mg, 0.27 mmol). The solution was heated to 100° C. for 20 hours, then cooled to room temperature, poured into water, and extracted with diethyl ether. The diethyl ether extract was washed with water, 5% ammonium hydroxide, water, and brine, then dried (magnesium sulfate), filtered and stripped to give a near colorless residue. The residue was flashed (Merck silica gel, 3% ethyl acetate in hexane) and the impure product was rechromatographed (Merck silica gel, 3% ethyl acetate in hexane) to afford essentially pure compound 3-B (2.990 gm, 99%) as a colorless oil.

Thin layer chromatography: $R_f=0.30$ (10% ethyl acetate in hexane).

3-C.
5-(1,1-Dimethylethyl)-4'-fluoro-3-(1methylethyl)[1,1'-biphenyl]-2-methanol

A cold (0° C.) solution of ester compound 3-B (2.920 gm, 8.5 mmol) in dry tetrahydrofuran (70 mL) was treated with lithium aluminum hydride (846 mg, 22 mmol). The ice bath was removed and the mixture was stirred at room temperature for 40 hours. The solution was then cooled to 0° C. and quenched in succession with water (0.8 mL), 10% sodium hydroxide (1 mL), and water (2.5 mL). The solution was filtered and the salts were washed with diethyl ether. The filtrate was stripped of solvent to afford a solid. The residue was dissolved in hot hexane and cooled to $-20°$ C, to provide compound 3-C (2.236 gm, 88%) as a white solid.

Melting point: 112°–114° C.

Thin layer chromatography: $R_f=0.39$ (20% ethyl acetate in hexane).

Microanalysis for $C_{20}H_{25}FO$: Calc'd.: C 79.96, H 8.39, F 6.32; Found: C 80.08, H 8.54, F 6.27.

3-D. 5-(1,1-Dimethylethyl)-4'-fluoro-3-(1methylethyl) [1,1'-biphenyl]-2-carboxaldehyde A $-78°$ C. solution of oxalyl chloride (821 $\mu$L, 1.19 gm, 9.4 mmol) in methylene chloride (20 mL) was treated dropwise with a solution of dry dimethylsulfoxide (1.35 mL, 1.49 gm, 19.0 mmol) in methylene chloride (1 mL). After 15 minutes, a solution of compound 3-C (2.175 gm, 7.24 mmol) in methylene chloride (7 mL) was added dropwise to the above mixture. Fifteen minutes after the addition, triethylamine (3.3 mL) was added and the mixture was stirred at $-78°$ C. for 5 minutes and then warmed to room temperature. The mixture was diluted with ethyl ether and washed with water, 1 N hydrochloric acid, water, and brine. The organic layer was dried (magnesium sulfate), filtered, and stripped to give a light yellow oil. The oil was chromatographed (flash, Merck silica gel, 3% ethyl acetate in hexane) to obtained slightly impure desired product as a solid. The solid was recrystallized from a minimum amount of hexane to give aldehyde Example 3 (1.681 gm, 78%) as white crystals.

Melting point: 84.5°–86.5° C.

Thin layer chromatography: $R_f=0.52$ (10% ethyl acetate in hexane).

EXAMPLE 4

(4-methyl-1-3-oxo-1-phenylpentyl)propanedioic acid diethyl ester

4-A. 4-Methyl-1-phenyl-1-penten-3-one

A solution of benzaldehyde (20.00 gm, 188 mmol) and methylisopropyl ketone (16.23 gm, 188.4 mmol) in absolute ethanol (100 mL) was treated with a solution of sodium ethoxide in ethanol (21% by weight, 9.70 gm, 30 mmol). After stirring at room temperature for 3 hours, most of the ethanol was removed on the rotovap and the residue was partitioned between diethyl ether and saturated ammonium chloride. The aqueous layer was removed and the diethyl ether layer was washed twice with water and once with brine, then dried (magnesium sulfate), filtered and stripped to give a liquid. The liquid was distilled (boiling point 91°–93° C. at 0.4 mm) to give compound 4-A as a pale yellow liquid (19.35 gm, 59%).

Thin layer chromatography: $R_f=0.50$ (20% ethyl acetate in hexane).

4-B. (4-methyl-1-3-oxo-1-phenylpentyl)propanedioic acid diethyl ester

A solution of compound 4-A (25.83 gm, 148.2 mmol) and diethyl malonate (33.24 gm, 207.5 mmol) in absolute ethanol (220 mL) was treated with a solution of sodium ethoxide in ethanol (21% by weight, 7.2 gm, 22 mmol). After stirring at room temperature for 16 hours, approximately 2 mL of acetic acid was added to the mixture and the ethanol was removed on the rotovap. The residue was dissolved in diethyl ether and the diethyl ether solution was washed with saturated ammonium chloride and brine, dried (magnesium sulfate), filtered and stripped. The resulting oil was transferred to a round bottom flask which was fitted with a short path distillation apparatus and subsequently heated at 90° C. and 0.5 mm in order to remove most of the unreacted diethyl malonate. The result was a crude 1,4-addition product (thin layer chromatography: $R_f=0.53$, 20% ethyl acetate in hexane).

EXAMPLE 5

3-Hydroxy-5-(1-methylethyl)[1,1-biphenyl]-4carboxylic acid, ethyl ester

5-A. (4-methyl-1-3-oxo-1-phenylpentyl)propanedioic acid

Crude 1,4 addition product compound 4-B was treated with a solution of potassium hydroxide (33.5 gm, 600 mmol) in water (200 mL) and enough ethanol was added to make the solution homogeneous. The mixture was refluxed for 45 minutes, during which time most of the ethanol was distilled off. The solution was cooled to room temperature and the aqueous solution was washed with diethyl ether. The diethyl ether layer was discarded and the aqueous layer was made acidic with concentrated hydrochloric acid (50 mL). The mixture was extracted with diethyl ether and the extract was washed with water and brine, then dried (magnesium sulfate), filtered and stripped to afford the crude intermediate diacid compound 5-A ($R_f=0.29$ in 8:1:1-methylene chloride:acetic acid:methanol) as an oil.

5-B. 6-Methyl-5-oxo-3-phenylheptanoic acid

A mixture of the crude diacid compound 5-A and cuprous oxide (2.1 gm, 14.7 mmol) was dissolved in acetonitrile (450 mL) and subsequently refluxed under argon for two hours. The cooled solution was stripped on the rotovap to remove nearly all of the acetonitrile. The residue was treated with water (100 mL) and 10% hydrochloric acid (100 mL) and the mixture was extracted with diethyl ether. The diethyl ether extract was washed with water and brine, then dried (magnesium sulfate), filtered and stripped to give a solid. The residue was recrystallized from ethyl acetate/hexane to afford compound 5-B (30.381 gm, 87% from compound 4-A) as a white powder.

Melting point: 103°–105° C.
Thin layer chromatography: $R_f=(1:1$-acetone: hexane).
Microanalysis for $C_{14}H_{18}O_3$: Calc'd.: C 71.77, H 7.74; Found: C 71.87, H 8.00.

5-C. 3,4-Dihydro-6-(1-methylethyl)-4-phenyl-2Hpyran-2-one and

5-D. Tetrahydro-6-(1-methylethylidene)-4phenyl-2H-pyran-2-one

Compound 5-B (3.000 gm, 12.8 mmol) was added as a solid to 50 mLs of a solution of ethyl acetate that was 1 M in acetic anhydride and 0.01 M in perchloric acid. After 5 minutes, the solution was diluted with diethyl ether and quenched with both saturated sodium bicarbonate and solid sodium bicarbonate. The organic layer was separated and washed with brine, then dried (magnesium sulfate), filtered and stripped to yield an oil. The oil was chromatographed (flash, Merck silica gel, 10% ethyl acetate in hexane) to give compound 5-C (1.705 gm, 62%) and compound 5-D (841 mg, 30%) as liquids.

For compound 5-C:
Thin layer chromatography: $R_f=0.41$ (20% ethyl acetate in hexane).
For compound 5-D:
Thin layer chromatography: $R_f=0.32$ (20% ethyl acetate in hexane).

5-E. 2-(1-Methylethyl)-6-oxo-4-phenyl-1-cyclohexene-1-carboxylic acid, ethyl ester A cold (0° C.) solution of isopropylcyclohexylamine (15.2 mL, 13.06 gm, 0.24 mmol) in dry tetrahydrofuran (180 mL) was treated with n-butyl lithium (2.5 M in hexane, 37 mL, 92.5 mmol). After stirring at 0° C. for 25 minutes and at room temperature for 5 minutes, the solution was cooled to −78° C. and treated dropwise with ethyl acetate (9.03 mL, 8.14 gm, 92.4 mmol). Thirty minutes after the addition, the mixture was added rapidly via cannula to a cold (0° C.) solution of compounds 5-C and 5-D (2:1 mixture, 10.000 gm, 46.23 mmol) in tetrahydrofuran (90 ml) and dimethylsulfoxide (70 mL). The mixture was stirred at 0° C. for 30 minutes, quenched with glacial acetic acid (75 mL), and stirred at room temperature for 16 hours. The tetrahydrofuran was removed on the rotovap and the residue was poured into diethyl ether and washed three times with water and once with brine. The solution was dried (magnesium sulfate), filtered and stripped to give an oil, which was redissolved in diethyl ether and washed again with water (twice) and brine, dried (magnesium sulfate), filtered and stripped. The resulting yellow oil (13.62 gm) was used directly in the next reaction.

5-F. 3-Hydroxy-5-(1-methylethyl)[1,1′-biphenyl]4-carboxylic acid, ethyl ester A mixture of the above oil 5-E and 2,3dichloro-5,6-dicyano-1,4-benzoquinone (15.74 gm, 69.3 mmol) in dry toluene (400 mL) was heated at 90° C. for 24 hours. The red mixture was cooled to room temperature, diluted with hexane and filtered to remove the precipitated solids. The filtrate was stripped and the dark residue was flashed (Merck silica gel, 10% diethyl ether in hexane) to give relatively pure product (5.216 gm) as a light brown oil that solidified on standing. The product was dissolved in hexane, concentrated to 15 mL and cooled to −20° C. to obtain Example 5 as off-white crystals (4.753 gm, 40% from 5-C and 5-D).

Melting point: 61°-62° C.

Thin layer chromatography: $R_f=0.41$ (20% ethyl ether in hexane).

Microanalysis for $C_{18}H_{20}O_3$: Calc'd.: C 76.03, H 7.09 Found: C 76.33, H 7.29.

EXAMPLE 6

4″-Fluoro-5′-(1-methylethyl)[1,1′:3′,1″-terphenyl]-4′-benzenecarboxaldehyde

6-A.

3-(1-Methylethyl)-5-[[(trifluoromethyl)sulfonyl]oxy][1,1′-biphenyl]-4-carboxylic acid, ethyl ester A cold (0° C.) solution of Example 5 (4.838 gm, 17.0 mmol) in dry pyridine (10 ml) was treated dropwise with trifluoromethanesulfonic anhydride (3.20 mL, 5.37 gm, 19.0 mmol). The red solution was stirred at 0° C. for one hour and at room temperature for 16 hours. The mixture was poured into water and extracted with diethyl ether. The diethyl ether extract was washed with water, 10% hydrochloric acid, water, and brine, then dried (magnesium sulfate), filtered and stripped. The residue was flashed (Merck silica gel, 10% ethyl acetate in hexane) to give compound 6-A (6.654 gm, 4%) as a colorless oil.

Thin layer chromatography: $R_f=0.49$ (20% ethyl acetate in hexane).

6-B.

4″-Fluoro-5′-(1-methylethyl)[1,1′:3′,1″-terphenyl]-4′-carboxylic acid, ethyl ester A mixture of compound 6-A (3.121 gm, 7.5 mmol), (4-fluorophenyl)-tri-n-butylstannane (4.343 gm, 11.3 mmol), lithium chloride (938 mg, 23.2 mmol), and a few crystals of 2,6-di-tertbutyl-4-methylphenol in dry dimethylformamide (35 mL) was treated with bis(triphenylphosphine) palladium dichloride (158 mg, 0.23 mmol). The solution was heated at 100° C. for 22 hours, cooled to room temperature, poured into water, and extracted with diethyl ether. The diethyl ether extract was washed with water, 5% ammonium hydroxide, water, and brine, and then dried (magnesium sulfate), filtered and stripped to give a light-colored residue. The residue was flashed (Merck silica gel, 10% ethyl acetate in hexane) and the impure product was rechromatographed (Merck silica gel, 7.5% ethyl acetate in hexane) to afford pure compound 6-B (2.529 gm, 93%) as a colorless viscous oil.

Thin layer chromatography: $R_f=0.31$ (90:5:5-hexane:toluene:ethyl ether).

6-C.

4″-Fluoro-5′-(1-methylethyl)[1,1′:3′,1″-terphenyl]-4′-methanol

A cold (0° C.) solution of ester compound 6-B (2.513 gm, 6.93 mmol) in dry tetrahydrofuran (80 mL) was treated with lithium aluminum hydride (800 mg, 21 mmol). The ice bath was removed and the mixture was stirred at room temperature for 16 hours. The solution was then cooled to 0° C. and quenched in succession with water (1 mL), 10% sodium hydroxide (1 mL), and water (3 mL). The solution was filtered and the salts were washed with diethyl ether. The filtrate was stripped of solvent to afford a solid. The residue was recrystallized from ethyl acetate/hexane to provide compound 6-C (1.913 gm, 86%) as a white solid.

Melting point: 153-°154.5° C.

Thin layer chromatography: $R_f=0.13$ (10% ethyl acetate in hexane).

Microanalysis for $C_{22}H_{21}FO$: Calc'd.: C 82.47, H 6.61, F 5.93 Found: C 82.20, H 6.51, F 5.85.

6-D.

4″-Fluoro-5′-(1-methylethyl)[1,1′:3′,1″terphenyl]-4′-benzenecarboxaldehyde

A −78° C. solution of oxalyl chloride (605 μL, 8.80 mg, 6.9 mmol) in methylene chloride (18 mL) was treated dropwise with a solution of dry dimethylsulfoxide (1.00 mL, 1.10 gm, 14.1 mmol) in methylene chloride (1 mL). After 15 minutes, a solution of compound 6-C (1.921 gm, 6.0 mmol) in methylene chloride (10 mL) and tetrahydrofuran (3 mL) was added dropwise to the above mixture. Fifteen minutes after the addition, triethylamine (4.0 mL) was added and the mixture was stirred at −78° C. for 5 minutes and then warmed to room temperature. The mixture was diluted with ethyl ether and washed twice with water and once with brine. The organic layer was dried (sodium sulfate), filtered, and stripped to give a solid residue. The residue was recrystallized from ethyl acetate/hexane to give aldehyde Example 6 (1.719 gm, 90%) as a white solid.

Melting point: 112°-113° C.

Thin layer chromatography: $R_f=0.51$ (20% ethyl acetate in hexane)

Microanalysis for $C_{22}H_{19}FO \cdot 0.15\ H_2O$: Calc'd.: C 82.29, H 6.06, F 5.92; Found: C 82.36, H 5.88, F 5.76.

EXAMPLE 7

4″-Fluoro-3″-methyl-5′-(1-methylethyl)[1,1′:3′,1″terphenyl]-4′-carboxaldehyde

7-A. 4″-Fluoro-3″-methyl-5′-(1-methylethyl)[1,1′:3′,1″-terphenyl]-4′-carboxylic acid, ethyl ester A mixture of compound 6-A (3.056 gm, 7.34 mmol), (4-fluoro-3-methylphenyl)-tri-n-butylstannane (4.982 gm, 12.5 mmol), lithium chloride (980 mg, 23.1 mmol), and a few crystals of 2,6di-tert-butyl-4-methylphenol in dry dimethylformamide (35 mL) was treated with bis(triphenylphosphine)palladium dichloride (158 mg, 0.23 mmol). The solution was heated at 100° C. for 25 hours, cooled to room temperature, poured into water, and extracted with diethyl ether. The ethyl ether was washed with water, 5% ammonium hydroxide, water, and brine, then dried (magnesium sulfate), filtered and stripped to give a near colorless residue. The residue was flashed (Merck silica gel, 5% ethyl acetate in hexane) and the impure product was chromatographed again (Merck silica gel, 6% ethyl acetate in hexane) to afford pure compound 7-A (2.251 gm, 81%) as a colorless viscous oil. Thin layer chromatography: $R_f=0.41$ (10% ethyl acetate in hexane).

7-B. 4″-Fluoro-3″-methyl-5′-(1-methylethyl)[1,1′:3′,1″-terphenyl]-4′-methanol

A cold (0° C.) solution of ester compound 7-A (2.237 gm, 5.94 mmol) in dry tetrahydrofuran (80 mL) was treated with lithium aluminum hydride (700 mg, 18.4 mmol). The ice bath was removed and the mixture was stirred at room temperature for 18 hours. The solution was then cooled to 0° C. and quenched in succession with water (1 mL), 10% sodium hydroxide (1 mL), and water (3 mL). The solution was filtered and the salts were washed with diethyl ether. The filtrate was stripped of solvent to afford a solid. The residue was recrystallized from ethyl acetate/hexane to provide compound 7-B (1.637 gm, 82%) as a white solid.

Melting point: 159°–160° C.

Thin layer chromatography: $R_f=0.14$ (ethyl acetate in hexane).

Microanalysis for $C_{23}H_{23}FO$: Calc'd.: C 82,60, H 6.93, F 5.68; Found: C 82.36, H 6.92, F 5.50.

7-C. 4''-Fluoro-3''-methyl-5'-(1-methylethyl)[1, 1':3', 1''-terphenyl]-4'-carboxaldehyde A −78° C. solution of oxalyl chloride (540 μL, 786 mg, 6.2 mmol) in methylene chloride (15 mL) was treated dropwise with a solution of dry dimethylsulfoxide (900 μL, 991 mg, 12.7 mmol) in methylene chloride (1 mL). After 15 minutes, a solution of compound 7-B (1.921 gm, 6.0 mmol) in methylene chloride (9 mL) and tetrahydrofuran (3 mL) was added dropwise to the above mixture. Fifteen minutes after the addition, triethylamine (3.5 mL) was added and the mixture was stirred at −78° C. for 5 minutes and then warmed to room temperature. The mixture was diluted with diethyl ether and washed successively with water (twice), 10% hydrochloric acid, water, and once with brine. The organic layer was dried (sodium sulfate), filtered, and stripped to give an oil. The residue was flashed (Merck silica gel, 5% ethyl acetate in hexane) to give aldehyde Example 7 (1.492 gm, 95%) as a colorless oil.

Thin layer chromatography: $R_f=0.48$ (10% ethyl acetate in hexane).

EXAMPLE 8

3,6-Dimethyl-5-oxoheptanoic acid 8-A.
(1,4-Dimethyl-3-oxopentyl)propanedioic acid, diethyl ester A cold (0° C.) solution of 2,2,6,6-tetramethylpiperdine (10.241 gm, 72.5 mmol) in tetrahydrofuran (120 mL) was treated with n-butyl lithium (2.5 M in hexane, 29.0 mL, 72.5 mmol). The light yellow solution was stirred at 0° C. for 30 . minutes, then cooled to −78° C. and treated with neat methyl isopropyl ketone (7.70 mL, 6.20 gm, 72 mmol) over a five-minute period. After 50 minutes, a solution of diethyl ethylidenemalonate (10.000 gm, 53.7 mmol) in tetrahydrofuran (7 mL) was added to the above mixture over a 10-minute period. After 50 minutes, the mixture was quenched with glacial acetic acid (5.0 ml) and warmed to room temperature. The mixture was poured into 50% saturated ammonium chloride and extracted with ethyl ether. The ethyl ether extract was washed with 1 N hydrochloric acid, water, and brine, then dried (magnesium sulfate), filtered and stripped to give a pale yellow oil. Distillation of the oil (P=0.15–0.2 mm Hg) afforded compound 8-A (10.883 gm, 74%) as a colorless liquid which boiled at 110°–114° C.

Thin layer chromatography: $R_f=0.25$ (20% ethyl acetate in hexane).

8-B. (1,4-Dimethyl-3-oxopentyl)propanedioic acid

A solution of diester 8-A (10.795 gm, 39.6 mmol) in ethanol (30 ml) was treated with a solution of potassium hydroxide (11.76 gm, 182 mmol) in water (60 mL). The mixture was refluxed for 1.5 hours, after which time most of the ethanol was distilled off. The solution was cooled to room temperature and the aqueous solution was washed with diethyl ether. The diethyl ether layer was discarded. The aqueous solution was made acidic with concentrated hydrochloric acid. The mixture was extracted twice with diethyl ether and the pooled extracts were washed with water and brine, then dried (magnesium sulfate), filtered and stripped to afford the crude intermediate diacid compound 8-B ($R_f=0.45$ in 8:1:1-methylene chloride:acetic acid:methanol) as a golden yellow oil.

8-C. 3,6-Dimethyl-5-oxoheptanoic acid

The crude diacid compound 8-B in acetonitrile (150 mL) was treated with cuprous oxide (601 mg, 4.2 mmol) and the mixture was subsequently refluxed under argon for 8 hours, then stirred at room temperature for 12 hours. The solution was stripped on the rotovap to remove nearly all of the acetonitrile. The residue was diluted with water and treated with 10% hydrochloric acid (20 mL), then extracted twice with diethyl ether. The pooled ethyl ether extracts were washed with water and brine, dried (magnesium sulfate), filtered and stripped to give acid Example 8 as a yellow oil (6.350 mg, 93%).

Thin layer chromatography: $R_f=0.36$ (1:1-acetone:hexane).

EXAMPLE 9

2-Hydroxy-4-methyl-6-(1-methylethyl)benzoic acid, ethyl ester

9-A.
3,4-Dihydro-4-methyl-6-(1-methylethyl)-2Hpyran-2-one and

9-B.
Tetrahydro-4-methyl-6-(1-methylethylidene)2H-pyran-2-one

A solution of compound 8-C (6.280 gm, 36.5 mmol) in ethyl acetate (15 mL) was added to a stirring solution of ethyl acetate (130 mL), acetic anhydride (14.6 gm, 143 mmol), and 70% perchloric acid (221 mg). After 5 minutes, the solution was diluted with diethyl ether and quenched with both saturated sodium bicarbonate and solid sodium bicarbonate. The organic layer was separated and washed with brine, then dried (magnesium sulfate), filtered and stripped to yield an oil. The oil was chromatographed (flash, Merck, silica gel, 10% ethyl acetate in hexane followed by 20% ethyl acetate in hexane) to give compounds 9-A (3.200 gn, 57%) and 9-B (1.788 gm, 32%) as colorless liquids. For compound 9-A:

Thin layer chromatography: $R_f=0.40$ (20% ethyl acetate in hexane). For compound 9-B:

Thin layer chromatography: $R_f=0.27$ (20% ethyl acetate in hexane).

9-C.
4-Methyl-2-(1-methylethyl)-6-oxo-1-cyclohexene-1-carboxylic acid, ethyl ester A cold (0° C.) solution of isopropylcyclohexylamine (10.2 mL, 8,76 gm, 62.0 mmol) in dry tetrahydrofuran (120 mL) was treated with n-butyl lithium (2.5 M in hexane, 25.0 mL, 62.5 mmol). After stirring at 0° C. for 25 minutes and at room temperature for 5 minutes, the solution was cooled to −78° C. and treated dropwise with ethyl acetate (6.1 mL, 5.50 gm, 62.4 mmol). Thirty minutes after the addition, the mixture was added rapidly via cannula to a cold (0° C.) solution of compounds 9-A and 9-B (1.6:1 mixture, 4.800 gm, 31.1 mmol) in tetrahydrofuran (60 mL) and dimethylsulfoxide (60 mL). The mixture was stirred at 0° C. for 40 minutes, quenched with glacial acetic acid (60 mL), and stirred at room temperature for 23 hours. The tetrahydrofuran was removed on the rotovap and the residue was poured into diethyl ether and washed three times with water. The aqueous layers were back-extracted once with diethyl ether and the pooled etheral layers were washed with brine. The solution was dried (magnesium sulfate), filtered and stripped to give an oil which was subjected to flash chromatography (Merck silica gel, 30% ethyl acetate in hexane), providing compound 9-C (6.035 gm, 87%) as a pale yellow oil.

Thin layer chromatography: $R_f=0.18$ (20% ethyl acetate in hexane).

9-D. 2-Hydroxy-4-methyl-6-(1-methylethyl)benzoic acid, ethyl ester

A mixture of compound 9-C (6.020 gm, 26.8 mmol) and 2,3-dichloro-5,6-dicyano-1,4benzoquinone (9.17 gm, 40.4 mmol) in dry toluene (250 mL) was heated at 90° C. for 21 hours. The solution was then cooled to room temperature, diluted with hexane and filtered through a plug of silica gel. The filtrate was stripped and the residue was flashed (Merck silica gel, 10% ethyl acetate hexane) to give pure phenol Example 9 (2.800 gm, 47%) as a colorless oil.

Thin layer chromatography: $R_f=0.48$ (20% ethyl acetate in hexane).

EXAMPLE 10

4'-Fluoro-3',5-dimethyl-3-(1-methylethyl)[1,1'biphenyl]-2-carboxaldehyde

10-A.
4-Methyl-2-(1-methylethyl)-6-[[(trifluoromethyl)sulfonyl]oxy]benzoic acid, ethyl ester A cold (0° C.) solution of phenol Example 9 (2.764 gm, 12.4 mmol) in dry pyridine (7 mL) was treated dropwise with trifluoromethanesulfonic anhydride (2.30 mL, 3.86 gm, 13.7 mmol). The solution was stirred at 0° C. for one hour and at room temperature for 17 hours. The mixture was poured into water and extracted with diethyl ether. The diethyl ether extract was washed with water, 10% hydrochloric acid, water, and brine, then dried (magnesium sulfate), filtered and stripped. The residue was flashed (Merck silica gel, 10% ethyl acetate in hexane) to give compound 10-A (3.938 gm, 90%) as a colorless oil.

Thin layer chromatography: $R_f=0.47$ (20% ethyl ether in hexane).

10-B. 4'-Fluoro-3',5-dimethyl-3-(1-methylethyl) [1,1'-biphenyl]-2-carboxylic acid, ethyl ester A mixture of compound 10-A (2.562 gm, 7.23 mmol), (4-fluoro-3-methylphenyl)-tri-n-butylstannane (4.150 gm, 10.4 mmol), and lithium chloride (960 mg, 22.7 mmol) in dry dimethylformamide (35 mL) was treated with bis(triphenylphosphine)palladium dichloride (160 mg, 0.23 mmol). The solution was heated at 100° C. for 7 hours, then cooled to room temperature, poured into water, and extracted with diethyl ether. The diethyl ether extract was washed with water, 5% ammonium hydroxide, water, and brine, then dried (magnesium sulfate), filtered and stripped to give a colorless residue. The residue was flashed (Merck silica gel, 5% ethyl acetate in hexane) and the impure product was re-chromatographed (Merck silica gel, 5% ethyl acetate in hexane) to afford pure compound 10-B (1.930 gm. 95%) as a colorless liquid.

Thin layer chromatography: $R_f=0.44$ (10% ethyl acetate in hexane).

10-C. 4'-Fluoro-3',5-dimethyl-3-(1-methylethyl) [1,1'-biphenyl]-2-methanol

A cold (0° C.) solution of ester compound 10-B (1.910 gm, 6.1 mmol) in dry tetrahydrofuran (60 mL) was treated with lithium aluminum hydride (848 mg, 22.3 mmol). The ice bath was removed and the mixture was stirred at room temperature for 16 hours. The solution was then cooled to 0° C. and quenched in succession with water (0.8 mL), 10% sodium hydroxide (1.4 mL), and water (2.8 mL). The solution was filtered and the salts were washed with diethyl ether. The filtrate was stripped of solvent to afford a solid. The residue was dissolved in hot hexane and cooled to provide compound 10-C (1.476 gm, 89%) as a white solid.

Melting point: 137.8–°138.4° C.

Thin layer chromatography: $R_f=0.37$ (20% ethyl acetate in hexane).

Microanalysis for $C_{20}H_{25}FO·0.1$ water: Calc'd.: C 78.86, H 7.79, F 6.93; Found: C 78.82, H 7.62, F 6.80.

10-D. 4'-Fluoro-3',5-dimethyl-3-(1-methylethyl) [1,1'-biphenyl]-2-carboxaldehyde A −78° C. solution of oxalyl chloride (600 μL, 873 mg, 6.9 mmol) in methylene chloride (11 mL) was treated dropwise with a solution of dry dimethyl sulfoxide (980 μL, 1.08 gm, 13.8 mmol) in methylene chloride (1 mL). After 15 minutes, a solution of alcohol compound 10-C (1.440 gm, 5.3 mmol) in methylene chloride (9 mL) was added dropwise to the above mixture. Twenty minutes after the addition, triethylamine (3.0 mL) was added and the mixture was stirred at −78° C. for 5 minutes and then warmed to room temperature. The mixture was diluted with diethyl ether and washed with water, 1 N hydrochloric acid, water, and brine. The organic layer was dried (magnesium sulfate), filtered, and stripped to give a liquid residue. The residue was chromatographed (flash, Merck silica gel, 4% ethyl acetate in hexane) to obtain aldehyde Example 10 (1.324 gm, 92%) as a colorless oil.

Thin layer chromatography: $R_f=0.51$ (10% ethyl acetate in hexane).

EXAMPLE 11

[3-(4-Fluorophenyl)-3-oxo-1-phenylpropyl]propanedioic acid, diethyl ester

11-A. 1-(4-Fluorophenyl)-3-phenyl-2-propen-1-one

A solution of benzaldehyde (19.220 g, 181 mmol) and p-fluoroacetophenone (25.000 g, 181 mmol) in ethanol (200 ml) was treated with sodium methoxide (1.972 g, 36.5 mmol). A precipitate fell out of solution after 30 minutes. After stirring at room temperature for 15 hours, the solution was treated with 50 ml of water, cooled in an ice bath, and filtered. The solid was rinsed with cold ethanol and dried under high vacuum to yield compound 11-A (29.730 g, 73%) as a yellow crystalline solid.

Melting point: 76.3°–77.5° C.

Thin layer chromatography: $R_f=0.46$ (20% ethyl acetate in hexane).

Microanalysis for $C_{15}H_{11}FO$: Calc'd.: C 79.63, H 4.90, F 8.40; Found: C 79.57, H 4.77, F 8.30.

11-B.
[3-(4-Fluorophenyl)-3-oxo-1-phenylpropyl]-propanedioic acid, diethyl ester A solution of compound 11-A (25.300 g, 111.8 mmol) and diethyl malonate (22.390 g, 140 mmol) in absolute ethanol (220 ml) was treated with a solution of sodium ethoxide in ethanol (21% by weight, 6.2 g, 19 mmol). After stirring at room temperature for 18 hours, approximately 1.3 ml of acetic acid was added to the mixture and the ethanol was removed on the rotovap. The residue was dissolved in diethyl ether and the diethyl ether solution was washed with 50% saturated ammonium chloride and brine, then dried with magnesium sulfate, filtered and stripped. The resulting oil was transferred to a round bottom flask fitted with a short path distillation apparatus and was subsequently heated at 85° C. at 0.2 mm in order to remove most of the unreacted diethyl malonate. The crude 1,4-addition product, Example 11 (43.635 g, 101% theory) was used directly in the next reaction.

EXAMPLE 12
4"-Fluoro-5'-hydroxy[1,1':3',1"-terphenyl]-4'carboxylic acid, ethyl ester

12-A. 4-Fluoro-γ-oxo-β-phenylbenzenepentanoic acid

A solution of crude compound 11-B in dioxane (80 ml) was treated with a solution of sodium hydroxide (13.4 g, 335 mmol) in water (100 ml). After stirring at room temperature for 1 hour, additional sodium hydroxide (6.2 g) in water (20 ml) was added and a thick slurry soon developed. The mixture was heated at 60° C. for 30 minutes, then cooled to room temperature and made acidic with concentrated hydrochloric acid. The mixture was extracted with diethyl ether and the diethyl ether layer was washed with water and brine, then dried (magnesium sulfate), filtered and stripped to afford the crude intermediate diacid ($R_f$=0.06 in 1:1-acetonone:-hexane) as a yellow oil.

A mixture of the crude diacid and cuprous oxide (1.30 g, 9.1 mmol) was dissolved in acetonitrile (300 ml) and subsequently refluxed under argon for 1.75 hours. The cooled solution was stripped on the rotovap to remove nearly all of the acetonitrile. The residue was treated with water and 10% hydrochloric acid and the mixture was extracted with diethyl ether. The diethyl ether extract was washed with water and subsequently extracted with 1 N sodium hydroxide (twice). The basic aqueous extracts were made acidic with concentrated hydrochloric acid and re-extracted with diethyl ether. The ethereal extract was washed with water and brine, then dried (magnesium sulfate), filtered and stripped to give a golden oil which solidified on standing. The residue was dissolved in hot ethyl acetate and triturated with hexane to give an oil which was cooled and seeded while swirling rapidly to afford analytically pure compound 12-A as a fine white solid (26.250 g, 82% from compound 11-A).

Melting point: 94.5°–96.° C.

Thin layer chromatography $R_f$=0.37 (1:1-acetone hexane)

Microanalysis for $C_{17}H_{15}FO_3$: Calc'd.: C 71 32, H 5.28, F 6.64; Found: C 71.45, H 5.17, F 6.44.

12-B.
6-(4-Fluorophenyl)-3,4-dihydro-4-phenyl2H-pyran-2-one

Compound 12-A (26.125 g, 91.2 mmol) was added as a solid to a solution of acetic anhydride (25 ml, 27.05 g, 265 mmol) and perchloric acid (72%, 370 mg) in ethyl acetate (230 ml). After 7 minutes, the solution was diluted with diethyl ether and quenched with both saturated sodium hydrogen carbonate and solid sodium hydrogen carbonate. The organic layer was separated and washed with brine, then dried (magnesium sulfate), filtered and stripped. The oil was chromatographed (flash, Merck silica gel, 1:1-methylene chloride:hexane) to give the product as a near colorless oil (22.870 g, 93%) which solidified on standing. Analytically pure compound 12-B was obtained by recrystallization from ethyl acetate/hexane.

Melting point: 74°–75.5° C.

Thin layer chromatography: $R_f$=0.35 (20% ethyl acetate in hexane).

Microanalysis for $CA_{17}H_{13}FO_2$: Calc'd.: C 76.11, H 4.88, F 7.08; Found: C 76.04, H 4.76, F 6.85.

12-C.
2-(4-Fluorophenyl)-6-oxo-4-phenyl-1-cyclohexene-1-carboxylic acid, ethyl ester A cold (0° C.) solution of isopropylcyclohexylamine (1.95 ml, 1.67 g, 11.6 mmol) in dry tetrahydrofuran (25 ml) was treated with n-butyl lithium (2.5 M in hexane, 4.7 ml, 11.75 mmol). After stirring at 0° C. for 30 minutes, the solution was cooled to −78° C. and treated dropwise with ethyl acetate (1.15 ml, 1.04 g, 11.8 mmol). Thirty minutes after the addition, the mixture was added rapidly via cannula to a cold (0° C.) solution of compound 12-B (1.500 g, 5.6 mmol) in tetrahydrofuran (12 ml) and dimethylsulfoxide (12 ml). The mixture was stirred at 0° C. for 40 minutes, quenched with glacial acetic acid (12 ml), and stirred at room temperature for 48 hours. The tetrahydrofuran was removed on the rotovap and the residue was poured into diethyl ether and washed three times with water and once with brine. The solution was dried (magnesium sulfate), filtered and stripped to give an oil, which was redissolved in diethyl ether, washed again with water (twice) and brine, dried (magnesium sulfate), filtered and stripped. The resulting yellow oil was chromatographed twice (Merck silica gel, 10% ethyl acetate in hexane for first, 6:3:1-hexane:-diethyl ether:toluene for second) to afford compound 12-C (1.150 g, 61%) as a colorless oil.

Thin layer chromatography: $R_f$=0.19 (20% ethyl acetate in hexane).

12-D
4"-Fluoro-5'-hydroxy[1,1':3',1"-terphenyl]4'-carboxylic acid, ethyl ester A mixture of compound 12-C (7.360 gm, 21.7 mmol) and 2,3-dichloro-5,6-dicyano-1,4benzoquinone (7.4 g, 32.6 mmol) in dry toluene (200 ml) was heated at 95° C. for 24 hours. The dark mixture was cooled to room temperature and filtered through a plug of silica gel. This silica gel was washed with 20% ethyl acetate in hexane and the filtrate was stripped to give a dark oil which rapidly solidified. The solid was dissolved in a mixture of methylene chloride and acetone and subjected to flash chromatography (Merck silica gel, 20% ethyl acetate in hexane) affording a brown solid. The solid was dissolved in diethyl ether and acetone, treated with decolorizing charcoal, and filtered to give a clear orange solution. Recrystallization of the resulting solid from ethyl acetate/hexane afforded pure compound 12-D (4.849 g, 66%) as light tan crystals. An additional 373 mg was obtained from the mother liquor to give a total of 5.222 g (72%) product.

Melting point: 116°-117.5° C.

Thin layer chromatography: $R_f = 0.44$ (20% ethyl acetate in hexane).

Microanalysis for $C_{21}H_{17}FO_3$: Calc'd.: C 74.99, H 5.09, F 5.65; Found: C 75.12, H 4.83, F 5.62.

EXAMPLE 13

5'-Ethenyl-4''-fluoro[1,1':3',1''-terphenyl]-4'carboxylic acid, ethyl ester

13-A.

4''-Fluoro-5'-[[(trifluoromethyl)sulfonyl]oxy][1,1':3',1''-terphenyl]-4'-carboxylic acid, ethyl ester A cold (0° C.) solution of compound 12-D (4.813 g, 14.3 mmol) in dry pyridine (9 ml) was treated dropwise with trifluoromethanesulfonic anhydride (2.65 ml, 4.44 g, 15.7 mmol). The dark solution was stirred at 0° C. for one hour and at room temperature for 19 hours. The mixture was poured into water and extracted with diethyl ether. The diethyl ether extract was washed with water, 10% hydrochloric acid (twice), water, and brine, then dried (magnesium sulfate), filtered and stripped. The residual oil was dissolved in methylene chloride and flashed (Merck silica gel, 10% ethyl acetate in hexane). The resulting solid was recrystallized from hexane to give analytically pure compound 13-A (6.168 g, 92%) as hard crystals.

Melting point: 94°-96° C.

Thin layer chromatography: $R_f = 0.48$ (20% ethyl acetate in hexane).

Microanalysis for $C_{22}H_{16}F_4O_5S$: Calc'd.: C 56.41, H 3.44, F 16.22, S 6.84; Found: C 56.55, H 3.26, F 15.94, S 7.01.

13-B.

5'-Ethenyl-4''-fluoro[1,1':3',1''-terphenyl]-4'-carboxylic acid, ethyl ester

A mixture of compound 13-A (600 mg, 1.28 mmol), vinyl(tri-n-butyl)tin (562 μl, 570.7 mg, 1.8 mmol), lithium chloride (177 mg, 4.2 mmol) and 2,6-di-tert-butyl-4-methylphenol (15 mg) in dimethylformamide (6.5 ml) was treated with bis(triphenylphosphine)palladium (II) dichloride (45 mg, 0.064 mmol) under argon. The mixture was quickly heated to 50° C. and then the temperature of the reaction mixture was slowly raised to 85° C. over a 2-hour period. After heating a total of 3 hours, the solution was cooled to room temperature, poured into diethyl ether, and washed in succession with water, 15% ammonium hydroxide, water, and brine, then dried (magnesium sulfate), filtered and stripped. The residue was subjected to flash chromatography (Merck silica gel, 10% ethyl acetate in hexane) to afford compound 13-B (400 mg, 90%) as a colorless oil.

Thin layer chromatography: $R_f = 0.51$ (20% ethyl acetate in hexane).

$^1$H-NMR (270 MHz, CDCl$_3$) δ1.02 (S,3H), 4.10 (q,2H), 5.42 (d,1H,J=11Hz), 5.84 (d,1H,J=17Hz), 6.93 (dd,1H,J=11,17Hz), 7.09 (t,2H), 7.34-7.50 (m,6H), 7.62 (m,2H), 7.78 (bs,1H).

EXAMPLE 14

5'-Ethyl-4''-fluoro[1,1':3',1''-terphenyl]-4'carboxylic acid, ethyl ester

A mixture of compound 13-A (600 mg, 1.28 mmol), tetraethyltin (380 μl, 451 mg, 1.92 mmol), lithium chloride (224 mg, 5.3 mmol) and 2,6-di-tert-butyl-4-methylphenol (14 mg) in dimethylformamide (6.5 ml) was treated with bis(triphenylphosphine)palladium (II)dichloride (45 mg, 0.064 mmol) under argon. The temperature of the reaction mixture was slowly raised to 100° C. over a 4-hour period. After 21 hours, the solution was cooled to room temperature, poured into diethyl ether, and washed in succession with water, 15% ammonium hydroxide, water, and brine, then dried (magnesium sulfate), filtered and stripped to give a dark oil. The residue was subjected to flash chromatography (Merck silica gel, 5% ethyl acetate in hexane) to afford Example 14 (368 mg, 83%) as a colorless oil.

Thin layer chromatography: $R_f = 0.56$ (20% ethyl acetate in hexane).

$^1$H-NMR (270 MHz, CDCl$_3$) δ1.02 (t,3H), 1.31 (t,3H), 2.79 (q,2H), 4.08 (q,2H), 7.08 (t,2H), 7.29-7.65 (m,9H).

EXAMPLE 15

4''-Fluoro-5'-methyl[1,1':3',1''-terphenyl]-4'carboxylic acid, ethyl ester

A cold (0° C.) slurry of copper iodide (370 mg, 1.94 mmol) in dry diethyl ether (5 ml) under argon was treated with methyl lithium (1.4 M) in diethyl ether, 2.75 ml, 3.85 mmol). Fifteen minutes after the addition, the clear solution was cooled to −78° C. and treated with a solution of compound 13-A (300 mg, 0.64 mmol) in diethyl ether (2 ml). The mixture was let slowly to warm to 0° C. and, after 2 hours, the solution was quenched with saturated ammonium chloride and 15% ammonium hydroxide. The reaction was extracted with diethyl ether and the ether layer was washed with 15% ammonium hydroxide, water, and brine, then dried (sodium sulfate), filtered and stripped to give a near colorless oil (210 mg). NMR analysis showed Example 15 was formed in 52% yield.

Thin layer chromatography: $R_f = 0.45$ (20% ethyl acetate in hexane).

$^1$H-NMR (270 MHz, CDCl$_3$) 67 1.03 (t,3H), 2.48 (s,3H), 4.11 (q,2H), 7.09 (t,2H), 7.28-7.67 (m,9H).

EXAMPLE 16

4''-Fluoro[1,1';3',1''-terphenyl]-4'-carboxylic acid, ethyl ester

A mixture of compound 13-A (300 mg, 0.64 mmol), tri-n-butylamine (460 μl 358 mg, 1.93 mmol), and bis(triphenylphosphine)palladium (II)dichloride (23 mg, 0.033 mmol) in dry dimethylformamide (1.3 ml) under argon was treated in one portion with formic acid (48.3 μl, 58.9 mg, 1.28 mmol). The mixture was subsequently heated at 100° C. for 3.5 hours, then cooled to room temperature, poured into diethyl ether, and washed in succession with water, 1 N hydrochloric acid, and brine, then dried (magnesium sulfate), filtered and stripped. The residue was subjected to flash chromatography (Merck silica gel, ethyl acetate in hexane) to afford Example 16 (199 mg, 97%) as a colorless oil.

Thin layer chromatography: $R_f = 0.46$ (20% ethyl acetate in hexane).

EXAMPLE 17

5'-(2-Ethoxyethenyl)-4"-fluoro[1,1':3',1"terphenyl]-4'-carboxylic acid, ethyl ester A mixture of compound 13-A (300 mg, 0.64 mmol), β-(ethoxyvinyl)tributyltin (349 mg, 0.97 mmol) lithium chloride (94 mg, 2.2 mmol) and 2,6-di-tert-butyl-4-methylphenol (15 mg) in dimethylformamide (3.3 ml) was treated with bis(triphenylphosphine)palladium(II) dichloride (25 mg, 0.036 mmol) under argon. The mixture was quickly heated to 50° C. and then the temperature of the reaction mixture was slowly raised to 85° C. over a 0.5 hour period. After heating a total of 1 hour, the solution was cooled to room temperature and stirred with 5% hydrochloric acid for 15 minutes. The mixture was then poured into diethyl ether and washed in succession with 5% hydrochloric acid, water, and brine. The ethereal layer was dried (magnesium sulfate), filtered and stripped. The residue was subjected to flash chromatography (Merck silica gel, 15% ethyl acetate in hexane) to afford the product as a solid. Recrystallization of the solid from hexane gave Example 17 as white crystals (197 mg, 79%).

Melting point: 120.1°–122.0° C.

Thin layer chromatography: $R_f$=0.35 (20% ethyl acetate in hexane).

Microanalysis for $C_{25}H_{23}FO_3$: Calc'd.: C 76.90, H 5.94, F 4.87; Found: C 76.90, H 5.90, F 4.82.

EXAMPLE 18

4"-Fluoro-5'-(phenylmethoxy)[1,1':3',1"-terphenyl]-4'-carboxylic acid, ethyl ester A mixture of Example 12 (105 mg, 0.312 mmol), benzyl bromide (75 μl, 108 mg, 0.63 mmol) and potassium carbonate (128 mg, 0.93 mmol) in dimethylformamide (1 ml) was stirred at room temperature for 4 hours. The solution was diluted with diethyl ether and washed with water and brine, then dried (sodium sulfate), filtered and stripped. The residue was subjected to flash chromatography (Merck silica gel, 10% ethyl acetate in hexane) to afford Example 18 (133 mg, 100%) as a colorless oil, which solidified on standing.

Melting point 79.5°–80.3° C.

Thin layer chromatography: $R_f$=0.39 (20% ethyl acetate in hexane).

EXAMPLES 19 TO 23

Examples 19 to 23 follow the formula

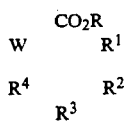

wherein W is as defined in the table below. In each of these examples, compound 13-A is treated under the conditions described in the table, following procedures described in the associated reference.

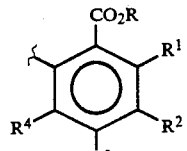

| Reaction Conditions | W | Reference |
|---|---|---|
| 19. Carbon monoxide, tributylstannane, tetrakis(triphenylphosphine)palladium, toluene or tetrahydrofuran, Δ | —CHO | Baillargeon, V. P.; Stille, J. K.; J. Am. Chem. Soc. 105 (1983), 7175–7176. |
| 20. Potassium cyanide, tetrakis triphenylphosphine) nickel (O), acetonitrile, Δ | —CN | Chambers, M. R. I.; Widdowson, D. A.; J. Chem. Soc., Perkin Trans. I (1989), 1365–1366. |
| 21. α-(Ethoxyvinyl)tributyltin, triphenylphosphine palladium(II) dichloride, toluene heat, followed by acidic aqueous work-up | —COCH$_3$ | Kosugi, M. et al., Bull. Chem. Soc. Japan, 60 (1987), 767–768. |
| 22. Carbon monoxide, R$^a$OH or R$^a$R$^b$NH, palladium catalyst, solvent (wherein R$^a$ and R$^b$ are each independently R$^1$, R$^2$, R$^3$, or R$^4$) | —CO$_2$R$^a$(NR$^a$R$^b$) | (a) Cacchi, S. et al., Tet. Lett., 1986, 3931–3934, (b) Dolle, R. E., J. Chem. Soc., Chem. Comm. (1987), 904–905. |
| 23. Nickel(II)chloride, Zinc metal, triphenylphosphine NaI, dimethylformamide, ultrasound | | Yamashita, J. et al., Chem. Lett. (1986), 407–408. |

EXAMPLE 24

Methyl(4-methyl-3-oxo-1-phenylpentyl)propanedioic acid, diethyl ester

A cold (0° C.) slurry of sodium hydride (60% in mineral oil, 5.28 g, 132 mmol) and methyl iodide (17 ml, 38.8 g, 273 mmol) in dry tetrahydrofuran (250 ml) was treated dropwise with a solution of compound 4-B (35.035 g, 104.8 mmol) in tetrahydrofuran (30 ml). After the addition, the mixture was slowly warmed to room temperature and stirred for 2.5 hours. The solution was quenched by the addition of saturated ammonium chloride and water and the mixture was extracted with diethyl ether. The ethereal layer was washed with brine, then dried (magnesium sulfate), filtered, and stripped to yield an oil. Flash chromatography of the oil (Merck silica gel, 20% ethyl acetate in hexane) afforded Example 24 (32.670 g, 89%) as a colorless oil. Thin layer chromatography: $R_f$=0.26 (20% ethyl acetate in hexane).

EXAMPLE 25

3-Hydroxy-2-methyl-5-(1-methylethyl)[1,1'biphenyl]-4-carboxylic acid, ethyl ester

25-A.
α-Methyl-β-(4-methyl-3-oxo-1-phenylpentyl)benzenepropanoic acid

A solution of Example 24 (32.52 g, 93.3 mmol) in 95% ethanol (130 ml was treated with a solution of potassium hydroxide (26.3 g, 411 mmol) in water (50 ml) and the mixture was refluxed for 2 hours. The clear-orange solution was concentrated on the rotovap and diluted with water. The aqueous solution was washed with diethyl ether. The diethyl ether layer was discarded and the aqueous layer was made acidic with concentrated hydrochloric acid. The mixture was extracted with diethyl ether and the extract was washed with water and brine, then dried (magnesium sulfate), filtered and stripped to afford the crude intermediate diacid ($R_f$=0.50 in 8:1:1-methylene chloride:acetic acid:methanol as an oil.

A mixture of the crude diacid and cuprous oxide (1.37 g, 9.6 mmol) was dissolved in acetonitrile (300 ml) and subsequently refluxed under argon for one hour. The cooled solution was stripped on the rotovap to remove nearly all of the acetonitrile. The residue was treated with water and 10% hydrochloric acid and the mixture was extracted with diethyl ether. The diethyl ether extract was washed with water and then extracted with 10% sodium hydroxide solution. The ethereal layer was discarded and the basic aqueous layer was made acidic with 10% hydrochloric acid and again extracted with diethyl ether. The diethyl ether extract was washed with water and brine, then dried (magnesium sulfate), filtered and stripped to give compound 25-A (14.99 g, 65%) as a pale yellow oil.

Thin layer chromatography: $R_f$=0.46 (1:1-acetone:-hexane; a mixture of diastereomers).

25-B.
3,4-Dihydro-3-methyl-6-(1-methylethyl)-4phenyl-2H-pyran-2-one

25-C
Tetrahydro-3-methyl-6-(1-methylethylidene)4-phenyl-2H-pyran-2-one

A solution of compound 25-A (14.94 g, 60.2 mmol) in ethyl acetate (30 ml) was added all at once to a mixture of acetic anhydride (23.3 g, 228 mmol) and perchloric acid (72%, 340 mg) in ethyl acetate (200 ml). After 7 minutes, the clear orange solution was diluted with diethyl ether and quenched with both saturated sodium hydrogen carbonate and solid sodium hydrogen carbonate. The organic layer was separated and washed with brine, then dried (magnesium sulfate), filtered and stripped to yield an oil. The oil was chromatographed (flash, Merck silica gel, 15% ethyl acetate in hexane) to give compounds 25-B and 25-C (12.09 g, 87%) as a complex mixture of four isomers.

Thin layer chromatography: $R_f$=0.54, 0.49, 0.44, 0.37 (20% ethyl acetate in hexane).

25-D.
5-Methyl-2-(1-methylethyl)-6-oxo-4-phenyl1-cyclohexene-1-carboxylic acid, ethyl ester A cold (0° C.) solution of isopropylcyclohexylamine (3.75 ml, 3.22 g, 22.8 mmol) in dry tetrahydrofuran (50 ml) was treated with n-butyl lithium (2.5 M in hexane, 9.12 ml, 22.8 mmol). After stirring at 0° C. for 25 minutes and at room temperature for 5 minutes, the solution was cooled to −78° C. and treated dropwise with ethyl acetate (2.20 ml, 1.98 g, 22.5 mmol). Thirty minutes after the addition, the mixture was added rapidly via cannula to a cold (0° C.) solution of compounds 25-B and 25-C (2.500 g, 10.86 mmol) in tetrahydrofuran (25 ml) and dimethylsulfoxide (25 ml). The mixture was stirred at 0° C. for 40 minutes, quenched with glacial acetic acid (25 ml), and stirred at room temperature for 3 days. The tetrahydrofuran was removed on a rotovap and the residue was poured into diethyl ether and washed three times with water and once with brine. The solution was dried (magnesium sulfate), filtered and stripped to give an oil which was chromatographed (flash, Merck silica gel, 10% ethyl acetate in hexane). Compound 25-D (1.812 g, 56%, a mixture of diastereomers) was obtained as a colorless oil.

Thin layer chromatography: $R_f$=0.33 0.30 (20% ethyl acetate in hexane). 25-E. 3-Hydroxy-2-methyl-5-(1-methylethyl)[1,1'biphenyl]-4-carboxylic acid, ethyl ester A mixture of compound 25-D (1.799 g, 6.0 mmol) and 2,3-dichloro-5,6-dicyano-1,4benzoquinone (2.04 g, 9.0 mmol) in dry toluene (50 ml) was heated at 100° C. for 24 hours. Additional 2,3-dichloro-5,6-dicyano-1,4benzoquinone (500 mg) was added and heating was continued for 5 more hours. The dark mixture was cooled to room temperature, diluted with hexane and filtered through a plug of silica gel. The silica gel was washed with 20% ethyl acetate in hexane and the filtrate was stripped and the dark residue was flashed (LPS-1, 4% ethyl acetate in hexane) to give compound 25-E (762 mg, 43%) as a colorless oil.

Thin layer chromatography: $R_f$=0.59 (20% ethyl acetate in hexane).

EXAMPLE 26

4''-Fluoro-2'-methyl-5'-(1-methylethyl[1,1': 3',1''terphenyl]-4'-carboxaldehyde

26-A.
2-Methyl-5-(1-methylethyl)-3-[[(trifluoromethyl]sulfonyl]oxy][1,1'-biphenyl]-4carboxylic acid, ethyl ester A cold (0° C.) solution of compound 25-E (3.363 g, 11.27 mmol) in dry pyridine (7 ml) was treated dropwise with trifluoromethanesulfonic anhydride (2.10 ml, 3.52 g, 12.5 mmol). The solution was stirred at 0° C. for 20 minutes and at room temperature for 19 hours. The mixture was poured into water and extracted with diethyl ether. The diethyl ether extract was washed with water, 10% hydrochloric acid, water, and brine, then dried (magnesium sulfate), filtered and stripped. The residue was flashed (Merck silica gel, 10% ethyl acetate in hexane) to give compound 26-A (4.692 g, 88%) as a colorless oil.

Thin layer chromatography: $R_f$=0.44 (10% ethyl acetate in hexane).

26-B. 4''-Fluoro-2'-methyl-5'-(1-methylethyl) [1,1':3',1''-terphenyl]-4'-carboxylic acid, ethyl ester A mixture of compound 26-A (4.444 g, 10.42 mmol), (4-fluorophenyl)-tri-n-butylstannane (8.027 g, 20.8 mmol, lithium chloride (1.57 g, 37.1 mmol) and a few crystals of 2,6-di-tertbutyl-4-methylphenol in dry dimethylformamide (28 ml) was treated with bis(triphenylphosphine) palladium (II) dichloride (308 mg, 0.44 mmol). The temperature of the solution was slowly raised to 95° C. over a 6-hour period and was subsequently heated at 95° C. for 48 hours. The solution was cooled to room temperature, poured into water, and extracted with diethyl ether. The diethyl ether was washed with water and brine, then dried (magnesium sulfate) filtered and stripped to give an oil. The residue was flashed (Merck silica gel, 90:5:5-hexane: diethyl ether:toluene) to afford pure compound 26-B (2.455 g, 60%) as a colorless oil. Thin layer chromatography: $R_f$=0.23 (90:5:5-hexane:diethyl ether:toluene).

26-C 4"-Fluoro-2'-methyl-5'-(1-methylethyl)[1,1': 3',1"-terphenyl]-4'-methanol A solution of ester 26-B (2.305 g, 6.12 mmol) in dry tetrahydrofuran (100 ml) was treated with lithium aluminum hydride (963 mg, 25.4 mmol). The mixture was stirred at room temperature for 24 hours then treated with additional lithium aluminum hydride (450 mg). After stirring at room temperature for 44 hours, the mixture was treated with more lithium aluminum hydride (500 mg) and was subsequently refluxed for 4 hours. The solution was then cooled to 0° C. and quenched in succession with water (2 ml), 10% sodium hydroxide (3 ml), and water (6 ml). The solution was filtered and the salts were washed with diethyl ether. The filtrate was stripped of solvent to afford a white foam which was chromatographed (flash, Merck silica gel, 20% ethyl acetate in hexane). Compound 26-C (1.883 g, 92%) was obtained as a white foam which solidified on standing.

Melting point: 127.5°–128.4° C.

Thin layer chromatography: $R_f=0.35$ (20% ethyl acetate in hexane).

26-D. 4"-Fluoro-2'-methyl-5'-(1-methylethyl[1,1':3',1"-terphenyl]-4'-carboxaldehyde A −78° C. solution of oxalyl chloride (610 μl, 888 mg, 7.0 mmol) in methylene chloride (14 ml) was treated dropwise with a solution of dry dimethylsulfoxide (1.00 ml, 1.10 g, 14.1 mmol) in methylene chloride (1 ml). After 15 minutes, a solution of alcohol 26-C (1.865 g, 5.58 mmol) in methylene chloride (4 ml) was added dropwise to the above mixture. Twenty minutes after the addition, triethylamine (3.5 ml) was added and the mixture was stirred at −78° C. for 5 minutes and then warmed to room temperature. The mixture was diluted with diethyl ether and washed with water, 1 N hydrochloric acid, water, and brine. The organic layer was dried (sodium sulfate), filtered and stripped to give a solid residue. The solid was dissolved in methylene chloride and flashed (Merck silica gel, 10% ethyl acetate in hexane) to give slightly impure Example 26. Recrystallization from hexane gave pure aldehyde Example 26 (1.693, 91%) as a white solid.

Melting point: 120.5°–121.5° C.

Thin layer chromatography: $R_f=0.57$ (20% ethyl acetate in hexane).

EXAMPLE 27

(3-Oxo-1-phenylbutyl)propanedioic acid, diethyl ester

A solution of sodium ethoxide in ethanol (21% by weight, 2.09 g, 0.031 mol) was added to a mixture of diethyl malonate (49.30 g, 0.307 mol) and trans-4-phenyl-3-buten-2-one (30.00 gm, 0.205 mol) in ethanol (500 ml) and was allowed to stir under argon at room temperature for 1.5 hours. The reaction was then quenched with acetic acid and concentrated to give an orange oil. The oil was dissolved in ether and washed with water, brine, dried over magnesium sulfate, filtered and concentrated to afford an orange oil. The oil was dissolved in hot ethyl acetate/hexane and cooled to give Example 27 as a pale yellow, crystalline solid (53.73 g, 86%).

Melting point: 38°–40° C.

Thin layer chromatography: $R_f=0.24$ (15% ethyl acetate in hexane).

EXAMPLE 28

3-Hydroxy-5-methyl[1,1'-biphenyl]-4-carboxylic acid, ethyl ester

28-A. (3-Oxo-1-phenylbutyl)propanedioic acid

A solution of potassium hydroxide (18.31 g, 0.327 mol) in water (150 ml) was added to a solution of Example 27 in ethanol (150 ml). The solution was allowed to reflux 5 hours. Ethanol was then distilled off. The remaining salt solution was cooled to room temperature and washed with ether. The aqueous layer was made strongly acidic with concentrated hydrochloric acid. The solution was extracted with ether (four times), the organic extracts were combined and washed with brine, dried over magnesium sulfate, filtered and concentrated to afford compound 28-A as a yellow oil which was used directly in the next reaction (17.87 g, 79%).

28-B. β-(2-Oxopropyl)benzenepropanoic acid

Diacid 28-A (17.87 g, 82 mmol) was dissolved in acetonitrile (250 ml), treated with cuprous oxide (1.17 g, 8.2 mmol) and allowed to reflux under argon for 3 hours. Additional cuprous oxide (0.58 g, 4.03 mmol) was added to the solution, which was allowed to reflux for an additional hour. The solution was then cooled to room temperature, concentrated, the residue diluted with water and treated with 10% hydrochloric acid (25 ml). The mixture was then extracted with ether (three times), the organic extracts were combined and washed with water (twice) and brine, then dried over magnesium sulfate, filtered and concentrated to afford a yellow oil which solidified upon standing. Product 28-B was recrystallized from ether/ethyl acetate/hexane to give hard beige crystals ((12.285 g, 86%).

Melting point: 77°–79° C.

Thin layer chromatography: $R_f=0.52$ (1:1, acetone:-hexane).

28-C. 3,4-Dihydro-6-methyl-4-phenyl-2H-pyran-2one

Compound 28-B (12.00 g, 58 mmol) was added as a solid to an ethyl acetate solution (200 ml), which was 1 M in acetic anhydride (20.04 g, 200 mmol) and 0.01 M in perchloric acid (70%, 0.228 g, 2 mmol). The solution was allowed to stir 15 minutes, then quenched carefully with saturated sodium hydrogen carbonate and solid sodium hydrogen carbonate. The organic layer was washed with brine, dried over magnesium sulfate, filtered and concentrated to a yellow oil. The oil was purified by flash chromatography on Merck silica gel in 20% ethyl acetate in hexane to afford cyclized ester compound 28-C as a colorless oil (10.20 g, 93%).

Thin layer chromatography: $R_f=0.55$ (20% ethyl acetate in hexane).

28-D. 2-Methyl-6-oxo-4-phenyl-1-cylcohexene-1carboxylic acid, ethyl ester

A 0° C. solution of isopropylcyclohexylamine (15.24 g, 108 mmol) in tetrahydrofuran (200 ml) was treated with 2.5 M n-butyl lithium (43.2 ml, 108 mmol) and allowed to stir 30 minutes under argon. The solution was warmed to room temperature over 5 minutes, then cooled to −78° C. and treated with dry ethyl acetate (9.51 g, 108 mmol). After stirring at −78° C. for 45 minutes, the solution was added via cannula to an ice cold solution of ester 28-C (10.20 g, 54 mmol) in tetrahydofuran (110 ml) and dimethylsulfoxide (80 ml).

After stirring at 0° C. for 45 minutes, the solution was treated with acetic acid (85 ml) and stirred 17 hours at room temperature. The solution was then concentrated and extracted with ether (twice), the organic layers were pooled and washed with water (three times) and brine, then dried over magnesium sulfate, filtered and concentrated to give a yellow oil. The oil was purified by flash chromatography on Merck silica gel in 10% ethyl acetate in hexane to afford pure product 28-D as a yellow oil (7.120 g, 43%).

Thin layer chromatography: $R_f=0.56$ (20% ethyl acetate in hexane).

28-E. 3-Hydroxy-5-methyl[1,1'-biphenyl]-4carboxylic acid, ethyl ester 2,3-Dichloro-5,6-dicyano-1,4-benzoquinone (14.88 g, 65.5 mmol) was added to a solution of ester 28-D (11.230 g, 43.69 mmol) in toluene and warmed slowly to 70° C. while stirring under argon. The solution was allowed to stir 7 hours at 70° C., then warmed to 80° C. and allowed to stir an additional 1.5 hours. The solution was then cooled to room temperature and filtered through a Celite ® pad, which was washed several times with hexane. The solution and washings were combined and concentrated to afford an orange oil. The oil was purified by flash chromatography on Merck silica gel in 1% ethyl acetate in hexane. Example 28 was obtained as an off-white, highly crystalline solid (3.015 g, 22%).

Melting point: 68°-69° C.

Thin layer chromatography: $R_f=0.68$ (15% ethyl acetate in hexane).

EXAMPLE 29

4''-Fluoro-3'',5'-dimethyl[1,1':3',1''-terphenyl]-4'-carboxaldehyde

29-A.
3-Methyl-5-[[(trifluoromethyl)sulfonyl]oxy][1,1'-biphenyl]-4-carboxylic acid, ethyl ester Trifluoromethanesulfonic anhydride (2.89 g, 10.23 mmol) was added dropwise to a solution of phenol Example 28 (3.015 g, 9.3 mmol) in pyridine (10 ml) while stirring under argon at 0° C.. After stirring 1 hour at 0° C., the solution was warmed to room temperature and allowed to stir for 21 hours. Another 0.1 equivalent of triflic anhydride (0.289 g, 1.023 mmol) was added to the solution, which was then allowed to stir an additional 30 minutes. The solution was then quenched with water and extracted with ether (three times). The combined organic layers were washed with water, 10% hydrochloric acid, water, and brine, dried over magnesium sulfate, filtered and concentrated to afford an orange residue. The residue was purified by flash chromatography, eluting with 10% ethyl acetate in hexane to afford compound 29-A as a clear oil (4.230 g, 100%).

Thin layer chromatography: $R_f=0.57$ (15% ethyl acetate in hexane).

29-B
4''-Fluoro-3'',5'-dimethyl[1,1':3',1''-terphenyl]-4'-carboxylic acid, ethyl ester Bis(triphenylphosphine)palladium chloride was added to a mixture of lithium chloride (0.972 g, 22.95 mmol), triflate 29-A (2.970 g, 7.65 mmol), 2,6-di-tert-butyl-4-methylphenol (trace), and (3-methyl-4-fluorophenyl)tri-nbutylstannane in dry dimethylformamide (25 ml) under argon at room temperature. The solution was then warmed to 100° C. and stirred for 17 hours. The solution was quenched with water and extracted with ether (three times). The organic layers were combined, washed with water, 10% ammonium hydroxide, water and brine, then dried over magnesium sulfate, filtered and concentrated to afford a yellow oil. This oil was purified by flash chromatography on Merck silica gel, eluting with 5% ethyl acetate in hexane. Those fractions containing pure product 29-B were combined and concentrated to give 0.940 g of a clear oil. A second flash chromatography of the combined and concentrated impure fractions of the first column was performed on Merck silica gel, eluting with 2% ethyl acetate in hexane, to give an additional 0.710 g of a clear oil. A third flash chromatography (identical conditions to second column) performed on the combined and concentrated impure fractions from the second column, afforded an additional 0.480 g of the ester 29-B as a clear oil (total, combined yield, 2.130 g, 80%).

Thin layer chromatography: $R_f=0.57$ (10% ethyl acetate in hexane).

29-C.
4''-Fluoro-3'',5'-dimethyl[1,1':3',1''-terphenyl]-4'-methanol

A tetrahydrofuran solution (20 ml) of ester 29-B (2.130 g, 6.12 mmol) was cooled to 0° C. and treated with lithium aluminum hydride (0.697 g, 18.36 mmol). After stirring for 15 minutes at 0° C., the solution was allowed to warm to room temperature and stirred for an additional 3 hours and 45 minutes. The solution was cooled to 0° C. and quenched by dropwise addition of 0.7 ml of water followed by 0.7 ml of 15% sodium hydroxide, then 2.1 ml water. The aluminum paste was filtered out of solution and the filtrate concentrated to afford a clear oil. The residue was dissolved in methylene chloride and purified by flash chromatography on Merck silica gel in 20% ethyl acetate in hexane. Alcohol 29-C was obtained as a clear oil (1.792 g, 92%).

Thin layer chromatography: $R_f=0.41$ (20% ethyl acetate in hexane).

29-D.
4''-Fluoro-3'',5'-dimethyl[1,1':3',1''-terphenyl]-4'-carboxaldehyde

Dimethylsulfoxide (0.912 g, 15.75 mmol) was added to a solution of oxalyl chloride (0.969 g, 7.64 mmol) in methylene chloride (30 ml) which had been cooled to −78° C. The solution was allowed to stir 20 minutes at −78° C. under argon. Compound 29-C (1.792 g, 5.87 mmol) was then added dropwise to the flask as a methylene chloride (5 ml) solution. 25 minutes later, triethylamine (4.08 ml, 40.4 mmol) was added dropwise. The solution was stirred for 20 minutes at −78° C., then warmed to room temperature. The solution was diluted with ether, washed with water and brine, then dried over sodium sulfate, filtered and concentrated to afford an orange oil. The compound was purified by flash chromatography on Merck silica gel in 5% ethyl acetate in hexane. Desired fractions were combined and concentrated to afford aldehyde Example 29 as a clear oil (1.435 g, 81%).

Thin layer chromatography: $R_f=0.62$ (10% ethyl acetate in hexane).

EXAMPLE 30

4''-Fluoro-5'-methyl[1,1':3',1''-terphenyl]-4'carboxaldehyde

30-A. 4''-Fluoro-5'-methyl[1,1':3',1''-terphenyl]4'-carboxylic acid, ethyl ester Bis(triphenylphosphine)palladium chloride (0.156 g, 0.223 mmol) was added to a mixture of lithium chloride (0.943 g, 22.3 mmol), triflate 29-A (2.80 g, 7.43 mmol), (3-methyl-4-fluorophenyl)tri-n-butylstannane (3.74 g, 9.71 mmol) and 2,6-di-tert-butyl-4-methylphenol (trace) in dry dimethylformamide (25 ml), stirring under argon at room temperature. The solution was then warmed to 100° C. and stirred for 22 hours. The solution was quenched with water and extracted with ether (five times). The organic layers were combined, washed with water, 10% ammonium hydroxide, water and brine, then dried over magnesium sulfate, filtered and concentrated to give a yellow oil. This oil was purified by flash chromatography on Merck silica gel in 10% ethyl acetate in hexane. Those fractions containing pure product 30-A were combined and concentrated to 1.940 g of a clear oil. A second flash chromatography of the combined and concentrated impure fractions of the first column were performed on Merck silica gel in 5% ethyl acetate in hexane to give an additional 0.455 g of the product as a clear oil (total, combined yield, 2.395 g, 97%). This product was identified as Example 15 (see above).

Thin layer chromatography: $R_f$=0.58 (15% ethyl acetate in hexane).

30-B. 4''-Fluoro-5'-methyl[1,1':3',1''-terphenyl]4'-methanol

A tetrahydrofuran solution (20 ml) of Example 15 (2.395 g, 7.17 mmol) was cooled to 0° C. and treated with lithium aluminum hydride (0.816 g, 21.51 mmol). After stirring for 30 minutes at 0° C., the solution was allowed to warm to room temperature and stirred for an additional 2 hours and 30 minutes. The solution was warmed to 50° C. for 5 minutes. The solution was then cooled to 0° C. and quenched by dropwise addition of 0.8 ml of water, followed by 0.8 ml of 15% sodium hydroxide, then 2.4 ml water. The aluminum paste was filtered out of solution and the filtrate concentrated to give a white foam which was recrystallized from ethyl acetate/hexane to give the desired alcohol 30-B as white crystals (1.795 g, 87%).

Melting point: 96°-98° C.

Thin layer chromatography: $R_f$=0.36 (20% ethyl acetate in hexane).

30-C. 4''-Fluoro-5'-methyl[1,1':3',1''-terphenyl]4'-carboxaldehyde

Dimethylsulfoxide (1.26 g, 16.16 mmol) was added to a solution of oxalyl chloride (1.025 g, 8.08 mmol) in methylene chloride (40 ml), which had been cooled to −78° C. The solution was allowed to stir for 20 minutes at −78° C. Alcohol 30-B (1.795 g, 6.21 mmol) was added dropwise to the flask as a methylene chloride (7 ml) solution. Twenty-five minutes later, triethylamine (4.32 ml, 42.78 mmol) was added dropwise and the solution was stirred for 10 minutes at −78° C., then warmed to room temperature. The solution was diluted with ether, washed with water (twice) and brine (once), dried over sodium sulfate, filtered and concentrated to afford an orange oil. The compound was purified by flash chromatography on Merck silica gel in 5% ethyl acetate in hexane. The desired fractions were combined and concentrated to afford a yellow solid which was recrystallized from ethyl acetate in hexane to give aldehyde Example 30 as pale yellow crystals (1.436 g, 81%).

Melting point: 86°-89° C.

Thin layer chromatography: $R_f$=0.17 (15% ethyl acetate in hexane).

What is claimed is:

1. A process for preparing a phenol ester of the formula

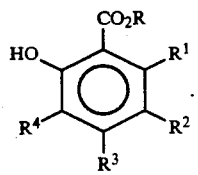

from a lactone substrate of the formula

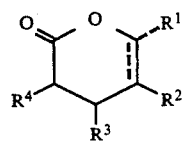

which comprises:
(a) reacting the substrate with an ester anion of the formula $X^1CH_2CO_2R$; and
(b) reacting the substrate with an oxidizing or dehydrogenating agent;

wherein:
R is lower alkyl;
$R^1$, $R^2$, $R^3$, and $R^4$ are each independently hydrogen, lower alkyl, cycloalkyl, aryl, aralkyl, or aralkoxy; and
$X^1$ is zinc halide or alkali metal.

2. The process of claim 1, wherein the lactone is first reacted with the ester anion to form a cyclohexenone ester of the formula

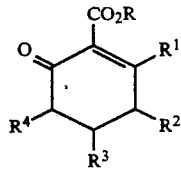

and then reacted with the oxidizing or dehydrogenating agent to form the phenol ester.

3. A process for preparing a phenol ester of the formula

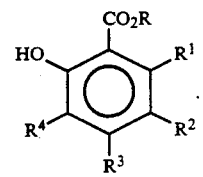

from a lactone of the formula

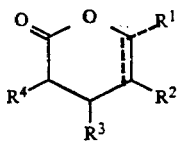

which comprises:

(a) reacting the lactone with an ester anion of the formula $X^1CH_2CO_2R$ to form a cyclohexanone of the formula

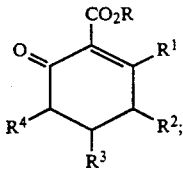

and (b) reacting the cyclohexenone with an oxidizing or dehydrogenating agent to form the phenol ester;

wherein:

R is lower alkyl;

$R^1$, $R^2$, $R^3$, and $R^4$ are each independently hydrogen, lower alkyl, cycloalkyl, aryl, aralkyl, or aralkoxy; and $X^1$ is zinc halide or alkali metal.

* * * * *